(12) United States Patent
Zhang et al.

(10) Patent No.: US 12,029,490 B2
(45) Date of Patent: Jul. 9, 2024

(54) LOW ENERGY PHOTOACOUSTIC MICROSCOPY (PAM) AND COMBINED PAM, DYE-BASED MICROSCOPY, AND OPTICAL COHERENCE TOMOGRAPHY

(71) Applicant: The Regents of the University of Michigan, Ann Arbor, MI (US)

(72) Inventors: Wei Zhang, Ann Arbor, MI (US); Xueding Wang, Ann Arbor, MI (US); Yannis Paulus, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 651 days.

(21) Appl. No.: 17/320,755

(22) Filed: May 14, 2021

(65) Prior Publication Data
US 2021/0353142 A1    Nov. 18, 2021

Related U.S. Application Data

(60) Provisional application No. 63/025,486, filed on May 15, 2020.

(51) Int. Cl.
| | |
|---|---|
| *A61B 3/13* | (2006.01) |
| *A61B 3/10* | (2006.01) |
| *A61B 5/00* | (2006.01) |
| *G02B 27/14* | (2006.01) |

(52) U.S. Cl.
CPC ............. *A61B 3/13* (2013.01); *A61B 3/102* (2013.01); *A61B 5/0095* (2013.01); *G02B 27/141* (2013.01)

(58) Field of Classification Search
CPC ......... A61B 3/13; A61B 3/102; A61B 5/0095; A61B 3/1233; A61B 3/1241; A61B 3/1225; A61B 3/14; A61B 3/18; A61B 5/0075; A61B 5/0035; A61B 5/7225; A61B 5/0066; G02B 27/141
USPC ........................................................ 351/205
See application file for complete search history.

(56) References Cited

PUBLICATIONS

Al-Amri et al., Optics in Our Time. Springer International Publishing, 2016. 509 pages.
Ameri et al., Natural course of experimental retinal vein occlusion in rabbit; arterial occlusion following venous photothrombosis. Graefes Arch Clin Exp Ophthalmol. Oct. 2008;246(10):1429-39.
American National Standards Institute, American national standard for safe use of lasers. Laser Institute of America, 2007. 22 pages.
American National Standards Institute, ANSI, "American National Standard for Safe Use of Lasers ANSI Z136. Jan. 2014," 2014. 23 pages.

(Continued)

*Primary Examiner* — Mohammed A Hasan
(74) *Attorney, Agent, or Firm* — Jason R. Bond; Casimir Jones, S.C.

(57) ABSTRACT

The present invention relates to systems for low-energy (e.g., 1.0 nJ-7.0 nJ) photoacoustic microscopy and methods for employing such systems. In certain embodiments, such systems employ a low-energy nanosecond pulsed laser beam (NPLB), at least two amplifiers, and a data acquisition system with at least three channels to generate at least three digital signals (e.g., which are averaged and normalized to the energy of the NPLB). In other embodiments, provided herein are systems for combined use of photoacoustic microscopy, dye-based microscopy (e.g., with fluorescein), and optical coherence tomography.

20 Claims, 11 Drawing Sheets
(11 of 11 Drawing Sheet(s) Filed in Color)

(56) References Cited

PUBLICATIONS

De Carlo et al., A review of optical coherence tomography angiography (OCTA). Int J Retina Vitreous. Apr. 15, 2015;1:5.

Elsner et al., Laser applications and system considerations in ocular imaging. Laser Photon Rev. Oct. 1, 2008;2(5):350-376.

Estorch et al., Future challenges of multimodality imaging. Recent Results Cancer Res. 2013;187:403-15.

Hajireza et al., In-Vivo functional optical-resolution photoacoustic microscopy with stimulated Raman scattering fiber-laser source. Biomed Opt Express. Jan. 16, 2014;5(2):539-46.

Holz et al., Medical retina: Focus on retinal imaging. Springer Science & Business Media, Berlin, 2010. TOC only. 21 pages.

Kumar et al., Detecting abnormalities in choroidal vasculature in a mouse model of age-related macular degeneration by time-course indocyanine green angiography. J Vis Exp. Feb. 19, 2014;(84):e51061. 7 pages.

Li et al., A new algorithm of multi-modality medical image fusion based on pulsecoupled neural networks. Advances in Natural Computation, 2015 pp. 995-1001.

Li et al., A novel model of persistent retinal neovascularization for the development of sustained anti-VEGF therapies. Exp Eye Res. Sep. 2018;174:98-106.

Liu et al., Optical coherence photoacoustic microscopy for in vivo multimodal retinal imaging. Optics letters, 2015, vol. 40:7. pp. 1370-1373.

Liu et al., Photoacoustic imaging of the eye: A mini review. Photoacoustics. May 18, 2016;4(3):112-123.

Manivannan et al., Ultra-wide-field fluorescein angiography of the ocular fundus. Am J Ophthalmol. Sep. 2005;140(3):525-7.

Martí-Bonmatí et al., Multimodality imaging techniques. Contrast Media Mol Imaging. Jul.-Aug. 2010;5(4):180-9.

Mrejen et al., Multimodal imaging of pigment epithelial detachment: a guide to evaluation. Retina. Oct. 2013;33(9):1735-62.

Mujat et al., High resolution multimodal clinical ophthalmic imaging system. Opt Express. May 24, 2010;18(11):11607-21.

Ng et al., Fundus fluorescein angiography in the screening for and management of retinopathy of prematurity. J Pediatr Ophthalmol Strabismus. Mar.-Apr. 2006;43(2):85-90.

Nguyen et al., High-resolution multimodal photoacoustic microscopy and optical coherence tomography image-guided laser induced branch retinal vein occlusion in living rabbits. Sci Rep. Jul. 22, 2019;9(1):10560.

Organisciak et al., Retinal light damage: mechanisms and protection. Prog Retin Eye Res. Mar. 2010;29(2):113-34.

Podoleanu et al., Optical coherence tomography. Br J Radiol. Nov. 2005;78(935):976-88.

Rosin et al., Multimodal retinal imaging: new strategies for the detection of glaucoma. International Conference on Image Processing, 3. 2002. III-III. 4 pages.

Schmitt, Optical coherence tomography (OCT): a review. IEEE Journal of selected topics in quantum electronics, 5. 1999. 1205-1215.

Schulmeister et al., Location and size of the apparent source for laser and optical radiation ocular hazard evaluation. ARC Seibersdorf research, A-2444. 2004. 9 pages.

Sharp et al., The scanning laser ophthalmoscope—a review of its role in bioscience and medicine. Phys Med Biol. Apr. 7, 2004;49(7):1085-96.

Slakter et al., Indocyanine-green angiography. Curr Opin Ophthalmol. Jun. 1995;6(3):25-32.

Song et al., Sound pressure level gain in an acoustic metamaterial cavity. Sci Rep. Dec. 11, 2014;4:7421.

Tian et al., Noninvasive chorioretinal imaging in living rabbits using integrated photoacoustic microscopy and optical coherence tomography. Opt Express. Jul. 10, 2017;25(14):15947-15955.

Tian et al., Novel Photoacoustic Microscopy and Optical Coherence Tomography Dualmodality Chorioretinal Imaging in Living Rabbit Eyes. J Vis Exp, vol. 132, 2018. p. e57135. 7 pages.

Wang et al., Noninvasive laser-induced photoacoustic tomography for structural and functional in vivo imaging of the brain. Nat Biotechnol. Jul. 2003;21(7):803-6.

Yang et al., Molecular contrast optical coherence tomography: a review. Photochem Photobiol. Mar.-Apr. 2005;81(2):215-37.

Yao et al., Photoacoustic Microscopy. Laser Photon Rev. Sep. 1, 2013;7(5).

Zaidi et al., Advances in multimodality molecular imaging. J Med Phys. Jul. 2009;34(3):122-8.

Zhang et al., High-resolution, in vivo multimodal photoacoustic microscopy, optical coherence tomography, and fluorescence microscopy imaging of rabbit retinal neovascularization. Light Sci Appl. Dec. 5, 2018;7:103.

Zhu et al., A novel multi-modality image fusion method based on image decomposition and sparse representation. Information Sciences, 432, 2018. 516-529.

LOW ENERGY PHOTOACOUSTIC MICROSCOPY (PAM) AND COMBINED PAM, DYE-BASED MICROSCOPY, AND OPTICAL COHERENCE TOMOGRAPHY

The present application claims priority to U.S. Provisional application Ser. No. 63/025,486, filed May 15, 2020, which is herein incorporated by reference in its entirety.

STATEMENT REGARDING FEDERAL FUNDING

This invention was made with government support under grant number K08EY027458 awarded by the National Institutes of Health. The government has certain rights in the invention.

FIELD OF THE INVENTION

The present invention relates to systems for low-energy (e.g., 1.0 nJ-7.0 nJ) photoacoustic microscopy and methods for employing such systems. In certain embodiments, such systems employ a low-energy nanosecond pulsed laser beam (NPLB), at least two amplifiers, and a data acquisition system with at least three channels to generate at least three digital signals (e.g., which are averaged and normalized to the energy of the NPLB). In other embodiments, provided herein are systems for combined use of photoacoustic microscopy, dye-based microscopy (e.g., with fluorescein, Rhodamine B, etc.), and optical coherence tomography.

BACKGROUND OF THE INVENTION

Due to the optical transparency of the eye, optical imaging methods are highly beneficial in the field of ophthalmology for diagnosis. Current clinically available optical imaging modalities include fundus photography, fluorescein angiography (FA) [1], indocyanine green angiography (ICDA) [2], optical coherence tomography (OCT) [3, 4], and scanning laser ophthalmoscopy (SLO) [5]. As a novel biomedical imaging method, photoacoustic microscopy (PAM) has the unique capability to non-invasively explore the optical absorption properties in biological tissues with high spatial resolution and deep penetration [6]. In PAM, a nanosecond-pulse-duration laser beam is used to induce localized thermoelastic tissue expansion. The thermoelastic wave emitted from the target area can be detected by an ultrasonic transducer(s) to extract the optical absorption information of the targeted area [7]. Previous publications have described the basic concept of PAM ocular imaging system, and investigated its potential applications and unique advantages in ophthalmic imaging [8-11].

Laser safety is an incredibly important aspect in ocular imaging. The transparent eye allows laser light transmission to the posterior segment, which also means that most of the laser energy will be directly delivered to the photoreceptors [12]. Since the photoreceptors, which are the neurons at the posterior portion of the retina, are extremely sensitive to light, the eye is particularly vulnerable to laser damage [13]. Although previous studies have suggested that PAM imaging of the eye can be achieved using laser fluence lower than the safety limits from the American National Standards Institute (ANSI) [9], laser safety remains to be a concern for potential clinical translation of this technology.

Since the eye is optically transparent and the retina can be easily accessed by light, ophthalmology has a long and rich legacy of benefiting from optical imaging methods for over 150 years[1], including fundus photography, fluorescein angiography (FA)[2, 3], indocyanine green angiography (ICGA)[4, 5], optical coherence tomography (OCT)[6-8], and scanning laser ophthalmoscopy (SLO)[9]. Fundus photography provides a rapid, wide field view of the retina in a single image capture; however, its depth-resolving capability is limited. By demonstrating the leakage of neovascularization, fundus FA remains the gold standard for evaluation and follow-up of neovascular diseases of the retina and choroid, such as proliferative diabetic retinopathy and. neovascular age-related macular degeneration, but it provides limited visualization of choroid. Although ICGA can reveal choroidal circulation, ICGA is invasive and requires the administration of an exogenous contrast agent. Obtaining a high resolution, three-dimensional retinal image with fluorescence imaging is challenging. OCT is able to image retinal morphology and retinal thickness by providing cross section and 3D anatomic images of the retina with high resolution. OCT angiography (OCTA) provides volumetric angiography image with the ability to demonstrate the blood flow information[10]. Both OCT and OCTA are limited by a relatively small field of view, inability to show leakage and limited view of microaneurysms, and image artifacts. Although SLO can capture almost the entire retina in one image, there is a conflict between the spatial resolution and the field of view[11].

Multi-modal retinal imaging is described as the use of more than one complementary technological system that is used to acquire images, concurrently or in a short period of time, for the purpose of diagnosis, prognostication, management, and monitoring of disease[12-15]. It takes the merits of the different modalities and compensates for their limitations, which will be highly beneficial to ophthalmology [16, 17]. Current multimodal retinal imaging performs each modality imaging sequentially and performs post-processing image registration given the limited eye fixation time. Although this method can provide the multi-modality information, it is limited by the eye fixation time, rapid eye saccades, and body motion which can increase the difficulty of performing image registration and increase image artifacts[18]. Different algorithms have been proposed to perform image fusion with the different modalities; the image stretching and warping will induce additional artifacts and uncertainties for diagnosis[19, 20].

Although previous studies described an integrated multi-modality imaging system, due to sharing the same laser system for different modalities, the three different modalities needed to be imaged sequentially. Since both PAM and FM share the same optical path, the system needed to be adjusted to avoid interference when shifted to different modalities [21]. The previous imaging system suffered from time consumption and distortion caused by body and eye motion artifacts. With sequential imaging in the previous system, it is difficult to perform image fusion and combine the advantages of different modalities.

SUMMARY OF THE INVENTION

The present invention relates to systems for low-energy (e.g., 1.0 nJ-7.0 nJ) photoacoustic microscopy and methods for employing such systems. In certain embodiments, such systems employ a low-energy nanosecond pulsed laser beam (NPLB), at least two amplifiers, and a data acquisition system with at least three channels to generate at least three digital signals (e.g., which are averaged and normalized to the energy of the NPLB). In other embodiments, provided herein are systems for combined use of photoacoustic microscopy, dye-based microscopy (e.g., with fluorescein, Rhodamine B, etc.), and optical coherence tomography.

In some embodiments, provided herein are systems comprising: a) a laser light source configured to generate an initial nanosecond pulsed laser beam (initial low-energy NPLB), wherein the initial low-energy NPLB is at a pulse energy level of between 1.0 nJ and 7.0 nJ (e.g., 1.0 ... 1.9 ... 2.7 ... 3.4 ... 5.0 ... 7.0); b) a beam splitter configured to split the initial low-energy NPLB into a transmitted low-energy NPLB and a reflected low-energy NPLB; c) a focusing assembly configured to direct the reflected low-energy NPLB into a designated area on or inside an object thereby causing localized thermoelastic expansion which generates ultrasonic waves; d) an ultrasonic transducer configured to detect the ultrasonic waves and generate a detected signal; e) a first amplifier (e.g., low noise amplifier) configured to amplify the detected signal to generate a first-amplified signal; f) a second amplifier (e.g., pulser-receiver) configured to amplify the first-amplified signal to generate a second-amplified signal; and g) a multi-channel data acquisition system (DAQ) comprising first, second, and third input channels each of which are configured to receive a portion of the second amplified signal such that first, second, and third digital signals are generated.

In certain embodiments, the systems further comprise: a processing system operably linked to the DAQ, wherein the processing system comprises: i) a computer processor, and ii) non-transitory computer memory comprising one or more computer programs, wherein the one or more computer programs, in conjunction with the computer processor and/or the DAQ, is/are configured to average the first, second, and third digital signals to generate an averaged digital signal. In other embodiments, the systems further comprise: a photodiode configured to measure the laser energy of the transmitted low-energy NPLD and generate a measured laser energy, and wherein the multi-channel DAQ is operably linked to the photodiode so as to receive the measured laser energy. In other embodiments, the one or more computer programs, in conjunction with a computer processor and/or the DAQ, is/are further configured to normalize the averaged digital signal using the measured laser energy to generate a normalized digital signal. In other embodiments, the system further comprises a median filter configured to generate a filtered signal from said normalized digital signal, and wherein said one or more computer programs, in conjunction with a computer processor and DAQ, is/are further configured to generate at least part of a PAM image from said filtered signal. In other embodiments, the system is configured to generate a multitude of normalized signals from a multitude of said initial low energy NPLBs, wherein said system further comprises a median filter configured to generate a multitude of filtered signals from said normalized digital signal, and wherein said one or more computer programs, in conjunction with a computer processor and DAQ, is/are further configured to generate a PAM image from said multitude of filtered signals.

In some embodiments, the DAQ further comprises a median filter that is configured to be applied to the normalized signal in the spatial domain. In other embodiments, the initial low energy NPLB is at a pulse energy level of between 1.5 nJ and 3.3 nJ. In additional embodiments, the initial low energy NPLB is at a pulse energy level of about 3.2 nJ. In further embodiments, the systems further comprise a spatial filter and attenuator which are receive and process the low energy NPLB prior to it encountering the beam splitter. In other embodiments, the low energy NPLB, after being processed by the filter and attenuator, comprises a Gaussian beam with a diameter of about 5 mm.

In some embodiments, the a focusing assembly comprises a two-axis scanning assembly and a telescope assembly configured to achieve a parallel beam from the reflected low-energy NPLB prior to the designated area of the object. In certain embodiments, the parallel beam has a diameter of about 1 mm. In additional embodiments, the focusing assembly further comprises an objective lens configured to focus the parallel beam on the designated area.

In certain embodiments, the designated area comprises biological tissue. In other embodiments, the biological tissue comprises eye tissue. In some embodiments, the eye tissue comprises corneal tissue. In additional embodiments, the initial low energy NPLB has a wavelength of between 450 nm and 900 nm. In some embodiments, the initial low energy NPLB has a wavelength of between 500 nm and 600 nm.

In some embodiments, the ultrasonic transducer comprises needle ultrasound transducer. In further embodiments, the ultrasonic transducer has a central frequency of between 15 and 40 (e.g., 15 ... 25 ... 40) MHz. In additional embodiments, the low-noise amplifier is a 55-65 dB low-noise amplifier.

In some embodiments, the systems further comprise a low-pass filter configured to filter the first-amplified signal prior to being amplified by the second amplifier (e.g., pulser-receiver). In other embodiments, the low-pass filter is at 30-34 MHz. In additional embodiments, the second amplifier (e.g., pulser-receiver) is further configured to have programmable gain. In other embodiments, the DAQ has a sampling rate of about 500 MHz set to about 24 dB. In certain embodiments, the DAQ is further configured to digitize the measured laser energy.

In particular embodiments, provided herein are methods comprising: a) activating a beam generating system such that a low-energy reflected nanosecond pulsed laser beam (NPLB) strikes a designated area on or inside an object causing localized thermoelastic expansion which generates ultrasonic waves, wherein the low-energy reflected NPLB has a pulse energy level of between 1.0 nJ and 7.0 nJ (e.g., 1.0 ... 1.9 ... 2.7 ... 3.4 ... 5.0 ... 7.0), and wherein the beam generating system comprises: i) a laser light source configured to generate an initial low-energy NPLB, ii) a beam splitter configured to split the initial low-energy NPLB into a transmitted low-energy NPLB and the reflected low-energy NPLB, and iii) a focusing assembly configured to direct the reflected low-energy NPLB into the designated area; b) detecting the ultrasonic waves with an ultrasonic transducer to generate a detected signal; and c) processing the detected signal with a signal processing system such that first, second, and third digital signals are generated, wherein the signal processing system comprises: i) a first amplifier (e.g, low-noise amplifier) that amplifies the detected signal to generate a first-amplified signal; ii) a second amplifier (e.g., pulser-receiver) that amplifies the first-amplified signal to generate a second-amplified signal; and iii) a multi-channel data acquisition device (DAQ) comprising first, second, and third input channels each of which receive at least a portion of the second amplified signal such that the first, second, and third digital signals are generated. In some embodiments, the method does not cause detectable damage to the designated area (e.g., eye of a subject). In particular embodiments, the steps above are repeated at least once per day for two, three, four, five, or six days (e.g., consecutive days, without causing detectable damage to the designated area (e.g., eye of a subject)).

In certain embodiments, the methods further comprise: d) processing the first, second, and third digital signals with a computer processing system operably linked to the DAQ, wherein the computer processing system comprises: i) a computer processor, and ii) non-transitory computer memory comprising one or more computer programs, and wherein the processing comprises averaging the first, second, and third digital signals to generate an averaged digital signal. In other embodiments, the beam generating system further comprises a photodiode, and wherein the method further comprises: measuring the laser energy of the transmitted low-energy NPLD with the photodiode to generate a measured laser energy. In further embodiments, the DAQ is operably linked to the photodiode and receives the measured laser energy from the photodiode. In some embodiments, the one or more computer programs, in conjunction with a computer processor and/or the DAQ, is/are further configured to normalize the averaged digital signal using the measured laser energy to generate an normalized digital signal. In some embodiments, the normalized digital signal is processed by a median filter to generate a filtered signal, and wherein said one or more computer programs, in conjunction with a computer processor and DAQ, generates at least part of a PAM image from said filtered signal. In certain embodiments, the method is repeated a multitude of times to generate a multitude of normalized signals, wherein said normalized digital signal is processed by a median filter to generate a multitude of filtered signals, and wherein said one or more computer programs, in conjunction with a computer processor and DAQ, generates a PAM image from said multitude of filtered signals.

In certain embodiments, the method is repeated a multitude of times (e.g., 10 . . . 50 . . . 100 . . . 1000 . . . 10,000) to generate a multitude of normalized signals, and wherein the one or more computer programs, in conjunction with a computer processor and DAQ, generates a PAM image from the multitude of normalized signals. In other embodiments, the DAQ further comprises a median filter that filters the normalized signal in the spatial domain. In other embodiments, the low energy reflected NPLB is at a pulse energy level of between 1.5 nJ and 3.3 nJ. In additional embodiments, the low energy reflected NPLB is at a pulse energy level of about 3.2 nJ.

In some embodiments, the beam generating system further comprising a spatial filter and attenuator which receive and process the low energy NPLB prior to it encountering the beam splitter. In further embodiments, the low energy NPLB, after being processed by the filter and attenuator, comprises a Gaussian beam with a diameter of about 5 mm. In some embodiments, the focusing assembly comprises a two-axis scanning assembly and a telescope assembly that produces a parallel beam from the reflected low-energy NPLB prior to the designated area of the object. In other embodiments, the parallel beam has a diameter of about 1 mm. In some embodiments, the focusing assembly further comprises an objective lens that focuses the parallel beam on the designated area.

In certain embodiments, the designated area comprises biological tissue (e.g., part of human body to be imaged). In other embodiments, the biological tissue comprises eye tissue. In further embodiments, the eye tissue comprises corneal tissue.

In particular embodiments, the initial low energy NPLB has a wavelength of between 450 nm and 900 nm. In some embodiments, the initial low energy NPLB has a wavelength of between 500 nm and 600 nm. In further embodiments, the ultrasonic transducer comprises needle ultrasound transducer. In particular embodiments, the ultrasonic transducer has a central frequency of between 15 and 40 MHz.

In some embodiments, the first amplifier (e.g., low-noise amplifier) is a 55-65 dB low-noise amplifier. In other embodiments, the signal processing system further comprises a low-pass filter that filters the first-amplified signal prior to being amplified by the second amplifier (e.g., pulser-receiver). In certain embodiments, the low-pass filter is at 30-34 MHz. In further embodiments, the second amplifier (e.g., pulser-receiver) is further configured to have programmable gain. In additional embodiments, the DAQ has a sampling rate of about 500 MHz set to about 24 dB. In other embodiments, the DAQ is configured to digitize the measured laser energy.

In some embodiments, provided herein are systems for simultaneous multi-modality imaging of an object comprising: a) a photoacoustic microscopy (PAM) sub-system comprising a PAM light source configured to generate PAM illumination light; b) a optical coherence tomography (OCT) sub-system comprising an OCT light source configured to generate OCT illumination light; c) a dye-based microscopy (DbM) sub-system comprising a DbM light source configured to generate DbM illumination light; d) a first dichroic mirror configured to coaxially align the PAM and DbM illumination lights; e) a dichroic beam splitter configured to couple the PAM and DbM illumination lights; f) a second dichroic mirror configured to coaxially align the OCT illumination light with the PAM and DbM illumination lights to generate a combined light, g) a galvanometer configured to reflect the combined light; h) a telescope assembly configured to deliver and focus the combined light to a designated area on or in an object to generate a PAM initial signal, a DbM initial signal, and an OCT initial signal; i) PAM, DbM, and OCT initial signal detectors configured to detect the PAM, DbM, and SD-OCT initial signals, and generate PAM, DbM, and OCT detected signals; j) a multi-channel data acquisition (mDAQ) sub-system configured to receive the PAM and DbM, detected signals, and generate PAM and DbM digital signals; k) an OCT data acquisition (oDAQ) sub-system configured to receive the OCT detected signal and generate an OCT digital signal; and l) a delay generator operably linked to the mDAQ and the oDAQ and configured to be triggered by at least one of the DbM, OCT, or PAM light sources to thereby activate and synchronize: i) the other two of the DbM, OCT, and PAM light sources; ii) the galvanometer, iii) the mDAQ sub-system, and iv) the oDAQ.

In certain embodiments, the designated area comprises a dye with a first emission wavelength. In other embodiments, the first dichroic mirror is further configured to remove all wavelengths from the PAM illumination light that are below the first wavelength of the dye. In additional embodiments, the PAM, DbM, and OCT illumination lights have wavelengths that do not overlap. In some embodiments, the illumination wavelength of the PAM, and the emission wavelength of the DbM and OCT, do not overlap. In additional embodiments, the optical coherence tomography is spectral domain optical coherence tomography (SD-OCT).

In some embodiments, the PAM initial signal detector comprises an ultrasound transducer. In other embodiments, the systems further comprise a low-noise amplifier configured to amplify the PAM detected signal. In some embodiments, the systems further comprise a processing system operably linked to the mDAQ and oDAQ, wherein the processing system comprises: i) a computer processor, and ii) non-transitory computer memory comprising one or more computer programs, wherein the one or more computer programs, in conjunction with the computer processor and/or the mDAQ and oDAQ, is/are configured to process the PAM, DbM, and OCT digital signals to generate PAM, DbM, and OCT 3D images of the designated area.

In particular embodiments, the one or more computer programs, in conjunction with the computer processor and/or the mDAQ and oDAQ, is/are further configured to align the PAM, DbM, and OCT 3D images to generate a 3D fusion image. In additional embodiments, the Z-axial plane of the OCT 3D image is employed as the standard to align to the DbM and OCT 3D images.

In some embodiments, provided herein are methods comprising: a) activating: i) a photoacoustic microscopy (PAM) system comprising a PAM light source to generate PAM illumination light, ii) an optical coherence tomography (OCT) system comprising an OCT light source to generate OCT illumination light, iii) a dye-based microscopy (DbM) system comprising a DbM light source to generate DbM illumination light, wherein the activating is under conditions such that the PAM, OCT, and DbM illumination lights are processed by a light handling system to generate a combined light that strikes a designated area on or in an object to generate PAM, DbM, and OCT initial signals, wherein the light handling system comprises a delay generator configured to be triggered by at least one of the DbM, OCT, or PAM light sources to thereby activate and synchronize the other two of the DbM, OCT, and PAM light sources; b) detecting the PAM, DbM, and OCT initial signals with PAM, DbM, and OCT initial signal detectors to generate PAM, DbM, and OCT detected signals; and c) processing the PAM, DbM, and OCT detected signals with a signal processing system such that PAM, DbM, and OCT digital signals are generated, wherein the signal processing system comprises a multi-channel data acquisition (mDAQ) system and an OCT data acquisition (oDAQ) system operably linked to the delay generator, wherein the mDAQ is configured to receive the PAM and DbM detected signals and generate the PAM and DbM digital signals, and the oDAQ is configured to receive the OCT detected signal and generate an OCT digital signal.

In some embodiments, the light handling system further comprises at least one of the following: i) a first dichroic mirror configured to coaxially align the PAM and DbM illumination lights, ii) a dichroic beam splitter configured to couple the PAM and DbM illumination lights; iii) a second dichroic mirror configured to: coaxially align the OCT illumination light with the PAM and DbM illumination lights to generate a combined light; iv) a galvanometer configured to reflect the combined light; and v) a telescope assembly configured to deliver and focus the combined light to the designated area on or in the object.

In further embodiments, the delay generator further activates and synchronizes the galvanometer and the mDAQ system and oDAQ system. In certain embodiments, the methods further comprise: d) processing the PAM, DbM, and OCT digital signals to generate PAM, DbM, and OCT 3D images of the designated area, wherein the processing is performed by a processing system operably linked to the mDAQ and oDAQ, wherein the processing system comprises: i) a computer processor, and ii) non-transitory computer memory comprising one or more computer programs.

In other embodiments, the one or more computer programs, in conjunction with the computer processor and/or the DAQ, align the PAM, DbM, and OCT 3D images to generate a 3D fusion image. In additional embodiments, the Z-axial plane of the OCT 3D image is employed as the standard to align to the DbM and OCT 3D images. In some embodiments, the designated area comprises a dye with a first emission wavelength. In additional embodiments, the first dichroic mirror removes all wavelengths from the PAM illumination light that would overlap with the first wavelength of the dye. In additional embodiments, the illumination wavelength of the PAM, and the emission wavelength of the DbM and OCT, do not overlap. In other embodiments, the PAM, DbM, and OCT illumination lights have wavelengths that do not overlap. In some embodiments, the optical coherence tomography is spectral domain optical coherence tomography (SD-OCT). In further embodiments, the PAM initial signal detector comprises an ultrasound transducer.

DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
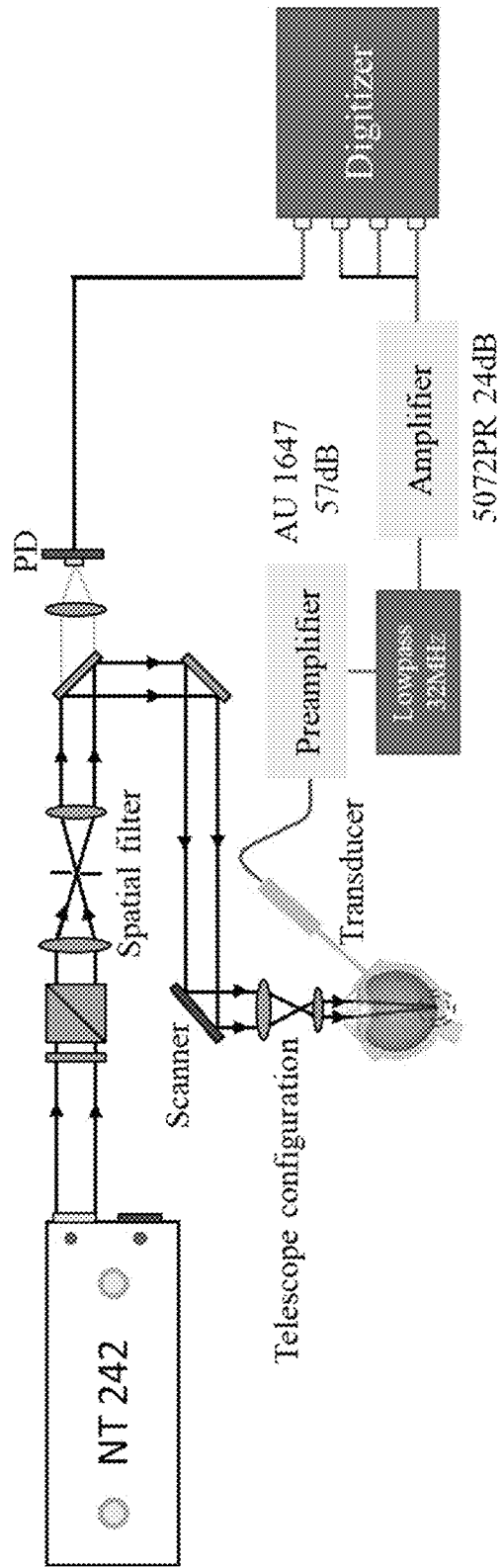
FIG. 1 shows an exemplary ultra-low energy PAM imaging and DAQ system.

The present invention relates to systems for low-energy (e.g., 1.0 nJ-7.0 nJ) photoacoustic microscopy and methods for employing such systems. In certain embodiments, such systems employ a low-energy nanosecond pulsed laser beam (NPLB), at least two amplifiers, and a data acquisition system with at least three channels to generate at least three digital signals (e.g., which are averaged and normalized to the energy of the NPLB). In other embodiments, provided herein are systems for combined use of photoacoustic microscopy, dye-based microscopy (e.g., with fluorescein), and optical coherence tomography.

First Exemplary Embodiment—Low Energy PAM

This first exemplary embodiment describes the use of an ultra-low energy PAM system, and the validation of its performance on rabbit eyes in vivo. A multi-channel data acquisition circuit with two-stage signal amplification was designed (see FIG. 1), which, in combination with the application of 3 by 3 median filter in the spatial domain, significantly improved the signal-to-noise ratio of the PAM system. Experiments performed on pigmented rabbits demonstrated that, when using this ultra-low energy PAM system, satisfactory image quality can be achieved in the eye with an incident laser fluence that is only 1% of the ANSI safety limit. Fundus photography and histology were performed after the imaging procedure, and no retinal or ocular damage was observed, demonstrating that exemplary PAM system has excellent safety.

Methods
System Design

Some of the core components for the PAM system are described in previous publications [8, 14] (both of which are herein incorporated by reference). The exemplary system is provided in FIG. 1. A spatial filter was placed after a tunable attenuator to achieve an approximate Gaussian beam with a diameter of 5 mm. The pulse to pulse laser energy was recorded by a photodiode through a beam splitter. A telescope configuration right after the two-axis scanning system was applied to achieve a parallel beam with 1 mm in diameter before the cornea, which led to a relatively small laser spot in retina area and minimized the variation in spot size caused by the change in distance between the objective lens and the eye. A laser wavelength of 578 nm where hemoglobin has a strong optical absorption was selected for imaging.

The generated photoacoustic signal was detected by a needle ultrasound transducer with a central frequency of 25.0 MHz (Optosonic Inc., Arcadia, CA, USA). The detected signal was first amplified by a 57-dB low-noise amplifier (AU-1647, L3 Narda-MITEQ, NY) and went through a low-pass filter (32 MHz, BLP-30+, Mini Circuits). The signal was then sent to a pulser/receiver (5072PR, Olympus) with programmable gain as the second stage amplifier. The further amplified signal was sent to three different channels of a multi-channel data acquisition (DAQ) system (PX1500-4, Signatec Inc, Newport Beach, CA) with a sampling rate of 500 MHz. To fully utilize the dynamic range of the DAQ system, the gain of the second stage amplifier was set to 24 dB, which also ensured that the maximal system noise would not go beyond 60% of the dynamic range of DAQ system. At the same time, the pulse-to-pulse laser energy monitored by the photodiode (PD) was digitized using the same DAQ card at the same sampling rate. The lateral resolution and the axial resolution of the PAM system were quantified as 4.1 μm and 37 μm, respectively [11].

Data Processing

The three signals acquired by the three channels of the multi-channel DAQ system were averaged. This step can enhance the SNR by a factor of $\sqrt{3}$ because the DAQ system noises associated with the three channels are independent. After this average, the signal was then normalized by the recorded laser energy to eliminate the variation due to the laser pulse energy fluctuation. To further enhance the SNR, a 3 by 3 median filter in the spatial domain was applied to the signals acquired over the 3D space. This step, although may slightly reduce the spatial resolution of the imaging system, could further enhance the SNR by removing the high-frequency noises. After these data processing steps, a PAM image was then assembled from the signals acquired via the point-by-point raster scan.

ANSI Safety Limit

By considering the combined effects of laser wavelength, exposure duration, repetition rate, illumination spot size, and pupil size, ANSI determined the laser safety standards for ocular exposure. The limits of the maximum permissible exposure (MPE) for the three types of illuminations include single pulse maximum permissible exposure ($MPE_{sp}$), average power MPE for thermal and photochemical hazard ($MPE_{average}$), and multiple-pulse MPE for thermal hazards ($MPE_{mp}$) [9, 15]. The $MPE_{sp}$ for single laser pulse energy is the most conservative among the three.

The retinal MPE value depends on the angular subtense of the apparent source α. In laser scanning ocular imaging, the angular subtense of the parallel beam is determined by the air-equivalent focal length of the eye and corresponding laser spot size in retina area, which should be around 17 mm and 20-25 µm, respectively [16, 17].

$$\alpha = \frac{25 \text{ µm}}{17 \text{ mm}} < \alpha_{min}$$

is achieved with intrabeam exposure of the eye by such a parallel Gaussian beam, where $\alpha_{min}$=1.5 mrad was defined by ANSI standard for safe use of lasers in ocular imaging [15]. The maximum permissible single laser pulse energy, $MPE_{sp}$, from a parallel Gaussian beam, as determined by the human pupil diameter of 7 mm, is 162 nJ [11].

Animal Handling

All the experimental procedures were performed in accordance with the ARVO (The Association for Research in Vision and Ophthalmology) Statement for the Use of Animals in Ophthalmic and Vision Research, and were approved by the Institutional Animal Care & Use Committee (IACUC) of the University of Michigan (Protocol PRO00008566, Photoacoustic & Molecular Imaging of the Eye). Five Dutch-belted pigmented rabbits (both genders, 3-4 months, 1.5-2.5 kg) were involved in this study. In briefly, the rabbits were first anesthetized with a mixed solution of ketamine (40 mg/kg) and xylazine (5 mg/kg) by intramuscular (IM) injection. The anesthesia was maintained by vaporized isoflurane anesthetic. The pupils of the eyes were dilated before performing the PAM imaging with 2.5% phenylephrine hydrochloride and 1% tropicamide ophthalmic solution. Topical anesthesia was used by 0.5% topical tetracaine drops prior to initiation of the experiments. The anesthesia level and rabbit state were monitored during the imaging procedure.

After all the PAM imaging procedure, the retina of each rabbit eye was checked using fundus photography to look for any possible damaged caused by the imaging procedure. Then the rabbit was euthanized by injection of intravenous injection of pentobarbital (Euthanasia solution, 0.22 mg/kg I.V, 50 mg/mL) (Intervet Inc., Madison, N.J., USA). The eyeballs were removed and fixed in Davidson's fixative solution (VWR, Radnor, Pa.) for 24-48 hours. The fixed tissues were cross-sectionally cut in 5-mm sections and embedded in paraffin. Subsequently, the paraffin-embedded tissues were sliced to a thickness of 5-6 µm and stained with hematoxylin and eosin (H&E) for standard histology.

Results

Imaging Experiments

FIG. 1 shows PAM images of retinal microvessels in a pigmented rabbit eye in vivo. (A)-(C) The images acquired by the ultra-low PAM system when using 1.6 nJ (1% of ANSI safety limit), 3.2 nJ (2% of ANSI safety limit, and 4.8 nJ (3% of ANSI safety limit) of pulse energy, respectively. (D) The image acquired by our original PAM system when using 20 nJ (13% of ANSI safety limit) of pulse energy. The performance of the ultra-low energy PAM system was tested by imaging the retinal blood vessels in the eyes of pigmented rabbits in vivo. Three different pulse energy levels, including 1.6 nJ, 3.2 nJ, and 4.8 nJ, which are at 1%, 2%, and 3% of the ANSI safety limit, respectively, were used in imaging. As shown in the FIGS. 2(A)-(C), at all the three energy levels, the PAM system can image the retina blood vessel with sufficient contrast-to-noise ratios. Even in the image acquired using 1.6 nJ energy (1% of the ANSI safety limit), microvessels in the retina can be recognized. The image quality was further improved when using higher pulse energy (3.2 nJ and 4.8 nJ), as demonstrated by additional vessels presented and the higher contrast-to-background ratios achieved. However, the differences in image quality by using 3.2 nJ and 4.8 nJ laser energy are very small, suggesting that, for the current application, there is no need to use laser pulse energy beyond 2% of the ANSI safety limit.

To further validate the improvement in performance, the same area in the rabbit retina was also imaged using the original PAM setup working with a laser pulse energy level of 20 nJ, as shown in FIG. 2(D). As reported in the previous publication [8], 20 nJ pulse energy, which is equivalent to 13% of the ANSI safety limit, was the lowest that could achieve acceptable image quality when using our original PAM setup. Compared to the image in FIG. 2(D), more microvessels (indicated by blue arrows) can be recognized in the image in FIG. 2(B). In addition, as shown in white dash box region, more details of retinal pigmented epithelium layer can be detected with our ultra-low energy PAM system. These improvements demonstrate that the ultra-low energy PAM system working with 3.2 nJ of pulse energy can achieve better imaging of retinal vessels than the original PAM system working with 20 nJ of pulse energy.

Figure 2:
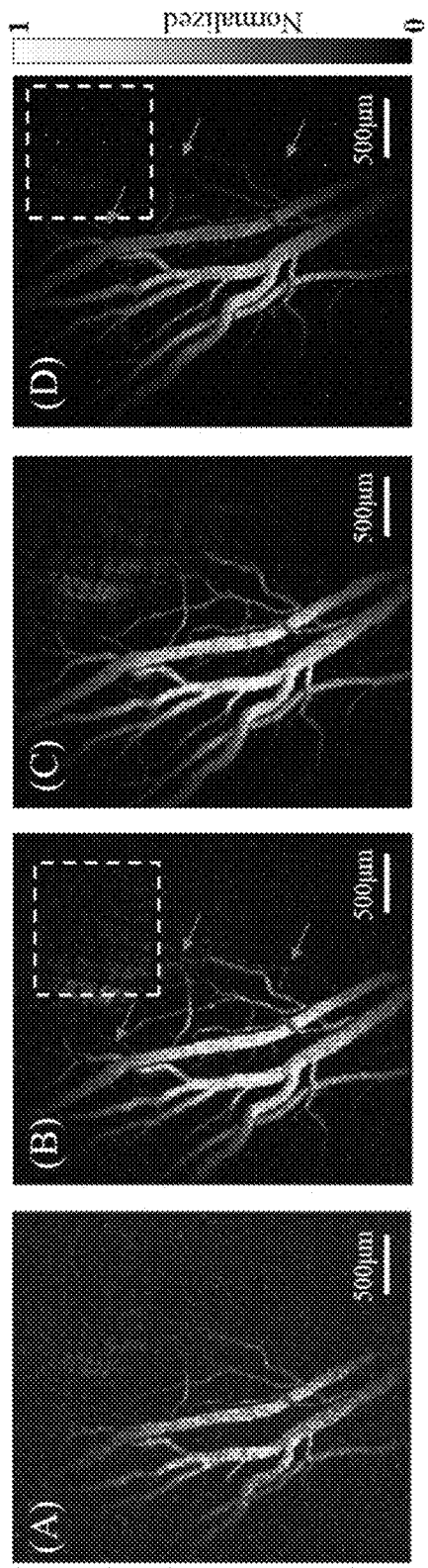
FIG. 2 shows PAM images of retinal micro vessels in a pigmented rabbit eye in vivo. (A)-(C) The images acquired by the exemplary ultra-low PAM system when using 1.6 nJ (1% of ANSI safety limit), 3.2 nJ (2% of ANSI safety limit, and 4.8 nJ (3% of ANSI safety limit) of pulse energy, respectively. (D) The image acquired by our original PAM system when using 20 nJ (13% of ANSI safety limit) of pulse energy.
Figure 3:
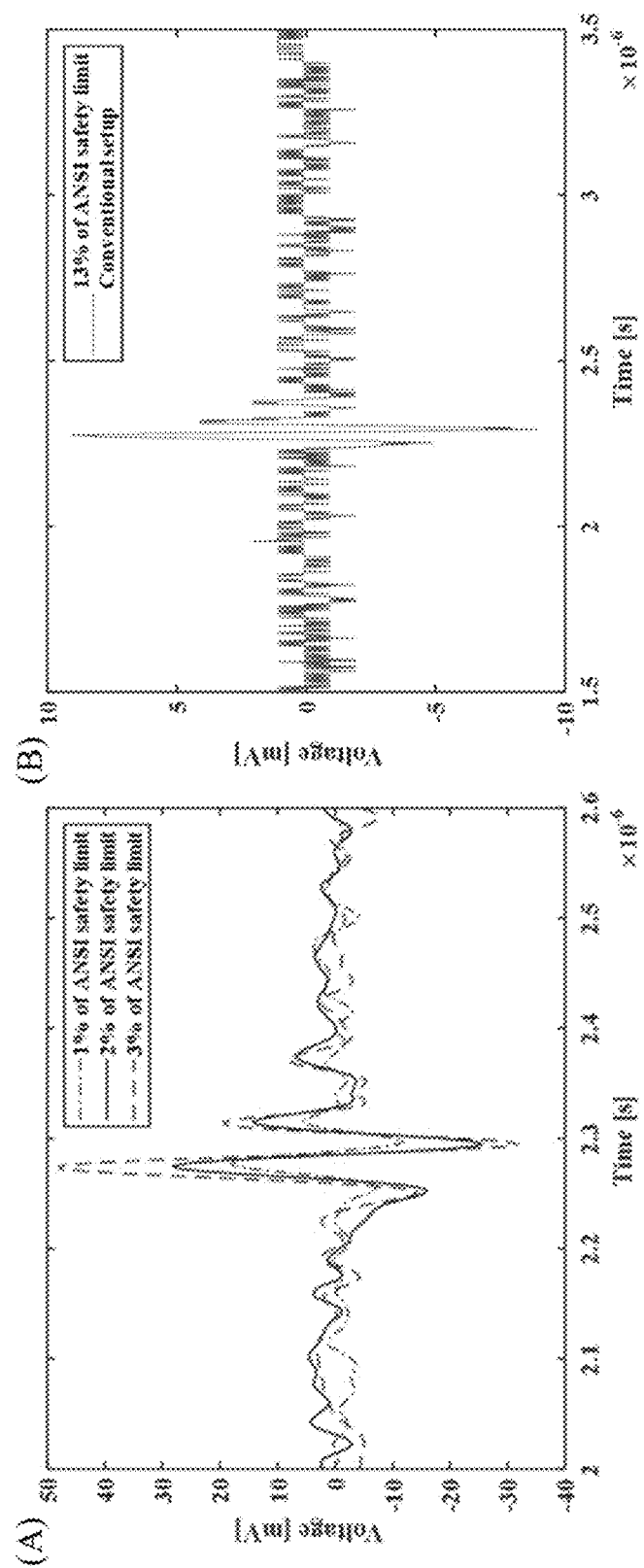
FIG. 3 shows A-scan signals from the first exemplary embodiment from the same location in the rabbit retina scanned by different setups when using different levels of laser pulse energy. (A) A-scan signals acquired by the ultra-low energy PAM system when using 1.6 nJ (1% of ANSI safety limit), 3.2 nJ (2% of ANSI safety limit), and 4.8 nJ (3% of ANSI safety limit) of pulse energy, respectively. (B) A-scan signal acquired by our original PAM setup when using 20 nJ (13% of ANSI safety limit) of pulse energy.

To further quantify the improvement in performance brought by the design, A-scan signals from the same location were extracted from volumetric scans leading to the imaging results in FIG. 2, and then the SNR was quantified from each of the extracted A-scan signal. FIG. 3(A) shows the A-scan signals from the same location scanned by the ultra-low energy PAM system when using 1.6 nJ (1% of ANSI safety limit), 3.2 nJ (2% of ANSI safety limit, and 4.8 nJ (3% of ANSI safety limit) of pulse energy, respectively. The quantified SNR are 3.2 dB, 5.8 dB, and 8.6 dB, respectively. FIG. 3(B) shows the A-scan signal from the same location scanned by our original PAM system when using 20 nJ (13% of ANSI safety limit) of pulse energy. The quantified SNR is 4.5 dB. As the SNR of PAM is proportional to the applied pulse energy, the estimated improvement in sensitivity brought by the new design is 9.2 folds.

Safety Evaluation

Figure 4:
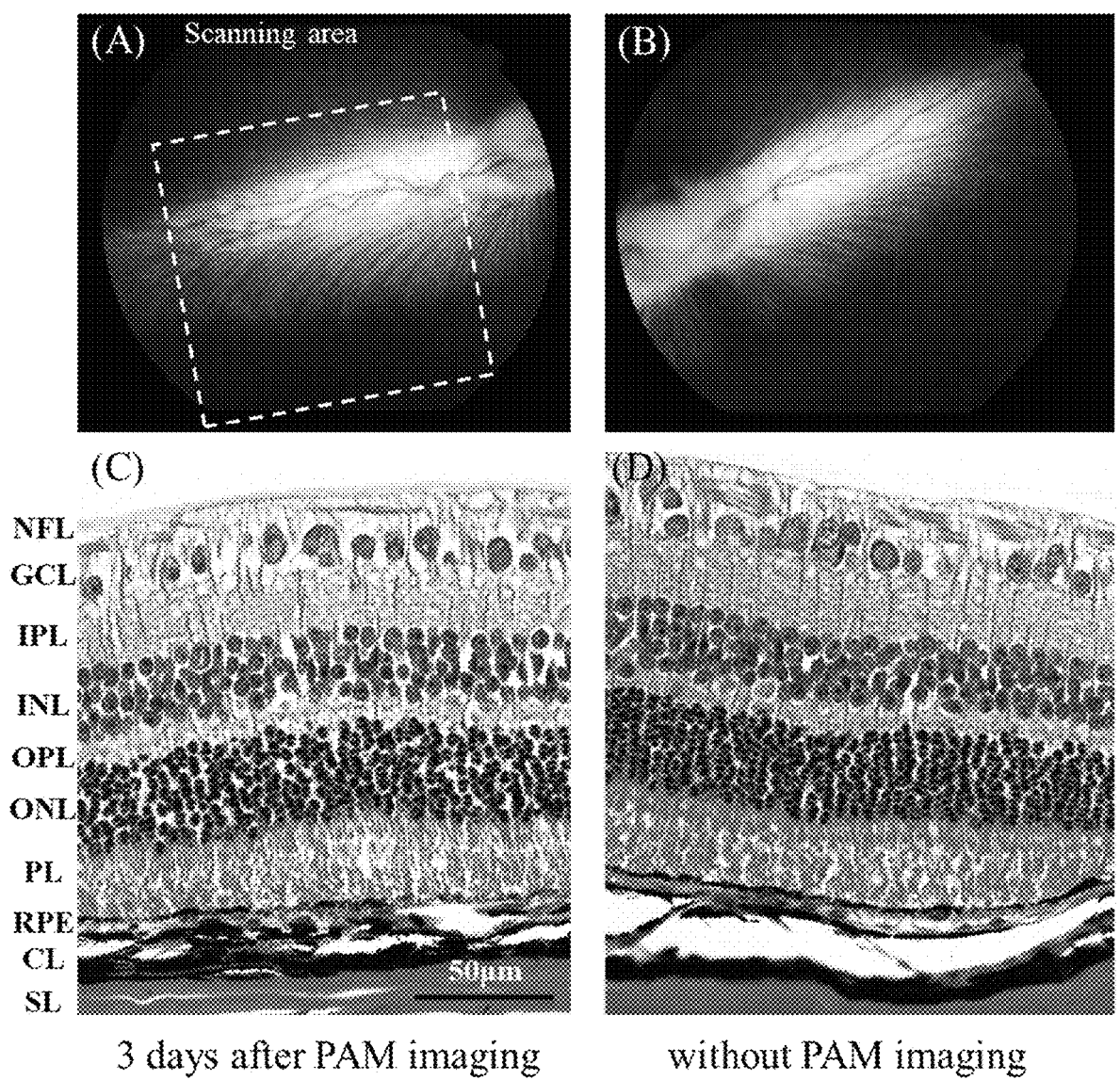
FIG. 4 shows results from a safety evaluation (of the first exemplary embodiment) using fundus photography and H&E stain histology. (A) Fundus photograph of the retina of a pigmented rabbit eye acquired 3 days after PAM imaging. (B) Fundus photograph of the retina of a pigmented rabbit eye before performing PAM imaging (control). (C) FA image of the retina of a pigmented rabbit eye acquired 3 days after PAM imaging. (D) FA image of the retina of a pigmented rabbit eye before performing PAM imaging (control). (E) H&E histology photograph of the retina of the pigmented rabbit eye scanned by PAM. (F) H&E histology photograph of the retina of the pigmented rabbit eye that was not imaged by PAM (control). The white dashed box marked the retina area that was scanned by PAM. NFL: nerve fiber layer; GCL: ganglion cell layer; IPL: inner plexiform layer; INL: inner nuclear layer; OPL: outer plexiform layer; ONL: outer nuclear layer; PL: photoreceptor layer; RPE: retinal pigment epithelium; CL: choroidal layer; SL: scleral layer.

Both fundus photography and histology were performed to evaluate possible laser damage in the pigmented rabbit eyes after performing the PAM imaging. The fundus photograph in FIG. 4(A) and the histology result in FIG. 4(C) were acquired 3 days after the rabbit receiving the PAM imaging. In this safety evaluation, the laser pulse energy used in PAM imaging was 3.2 nJ (2% of ANSI safety limit). The retinal area scanned by PAM had a size of 7 mm by 7 mm, as marked by the white dashed box in FIG. 4(A). This area was also the one that was sectioned for histology examination. To be used as a control, the eye of another pigmented rabbit without being scanned by PAM was also examined by the same procedure of fundus photography and histology, as the results shown in FIGS. 4(B) and (D). Compared to the results from the control, the safety evaluation results from the rabbit eye acquired 3 days after PAM imaging do not show any detectable difference. Neither on the fundus photograph nor on the H&E histology photograph, we can see any noticeable damage in the tissues that were scanned by PAM.

This exemplary embodiment presents an ultra-low energy PAM system that could be used for ophthalmic imaging or other tissue engineering. This system achieved by PAM a very low laser pulse energy of only 1% of the ANSI safety limit. By applying the two-stage signal amplification and multi-channel data acquisition, the dynamic range of the DAQ system was fully utilized, which helped to distinguish much more details in the detected signal. In addition, by applying a 3 by 3 spatial-domain based median filter, the acquired signals was averaged at each time point to further reduce the system noise. Combining the signal average over the multiple channels in the DAQ system and the data processing procedure, each A-scan received an equivalent of a total average of 27 times. This average, unlike the time-domain signal average utilized in many previous studies to enhance the sensitivity of PAM, is not performed over multiple laser pulses and, therefore, does not sacrificed the imaging speed or raises safety concerns of multiple pulse exposure.

Experiments conducted on pigmented rabbit eyes in vivo demonstrated that the newly designed system and data processing method can significantly reduce the laser pulse energy required for imaging retinal vasculature. Although the image acquired with the pulse energy at 2% of ANSI safety limited shows better result, most of the retinal blood vessel can be clearly distinguished when using the pulse energy at 1% of ANSI safety limit. Compared with other PAM systems developed and used in other studies [8, 11], the pulse energy required for ocular imaging was reduced by 20nJ/1.6nJ=12.5 times. The excellent safety of the ultra-low energy PAM system for retinal imaging was validated by fundus photography and H&E stained histology conducted on the rabbit eyes at 3 days after PAM imaging. The results from both tests confirmed that the PAM imaging working with laser pulse energy at 2% of ANSI safety limit did not induce any noticeable damage in the pigmented rabbit eye.

Second Exemplary Embodiment—Combined PAM, Dye-Microscopy, and OCT

This second exemplary embodiment describes development of a multi-modality eye imaging system and evaluating its feasibility of acquiring images of different modalities simultaneously. An integrated multimodality imaging system combining spectral-domain optical coherence tomography (SD-OCT), photoacoustic microscopy (PAM), and dye based microscopy (DM, called "FM" when fluorescent dye used) was developed, and its performance for eye imaging was validated on multiple clinically-relevant retinal disease models in vivo in rabbits. OCT imaging allows for visualization of the different anatomic retinal layers with high axial resolution. PAM can be used to image vasculature, angiogenesis, and hemorrhages. The leakage of neovascularization can be verified with DM and fluorescein dye. Simultaneous imaging with OCT, PAM, and DM (e.g., FM) ensures co-registration of the three modalities without being affected by motion artifacts caused by breathing, body or eye movements, and heartbeat.

Methods
System Setup

Figure 5:
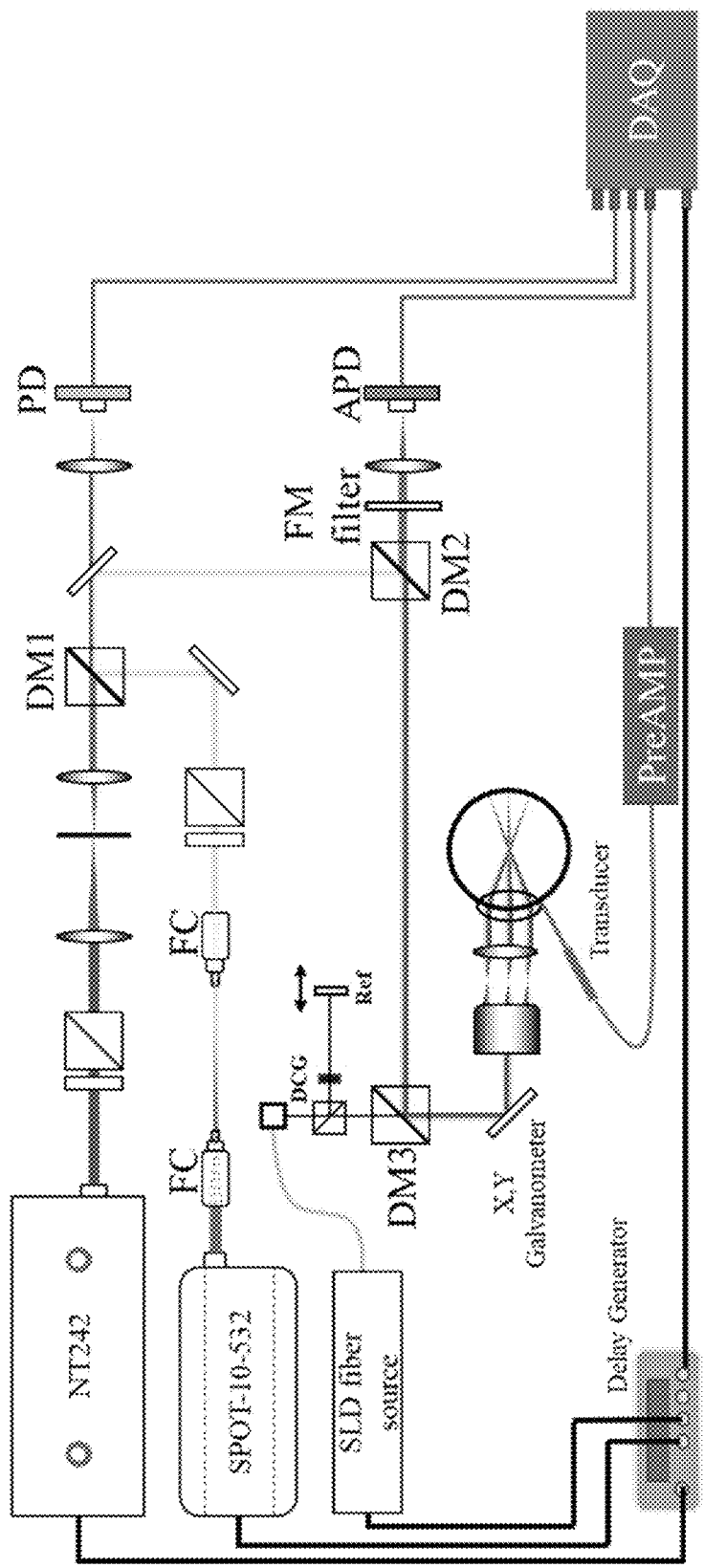
FIG. 5 shows the experimental setup for the second exemplary embodiment for simultaneous multi-modality retina imaging with integrated spectral-domain OCT (SD-OCT), PAM, and FM. (FC: fiber collimator, DM: dichroic mirror, DCG: dispersion compensation glass).
Figure 6:
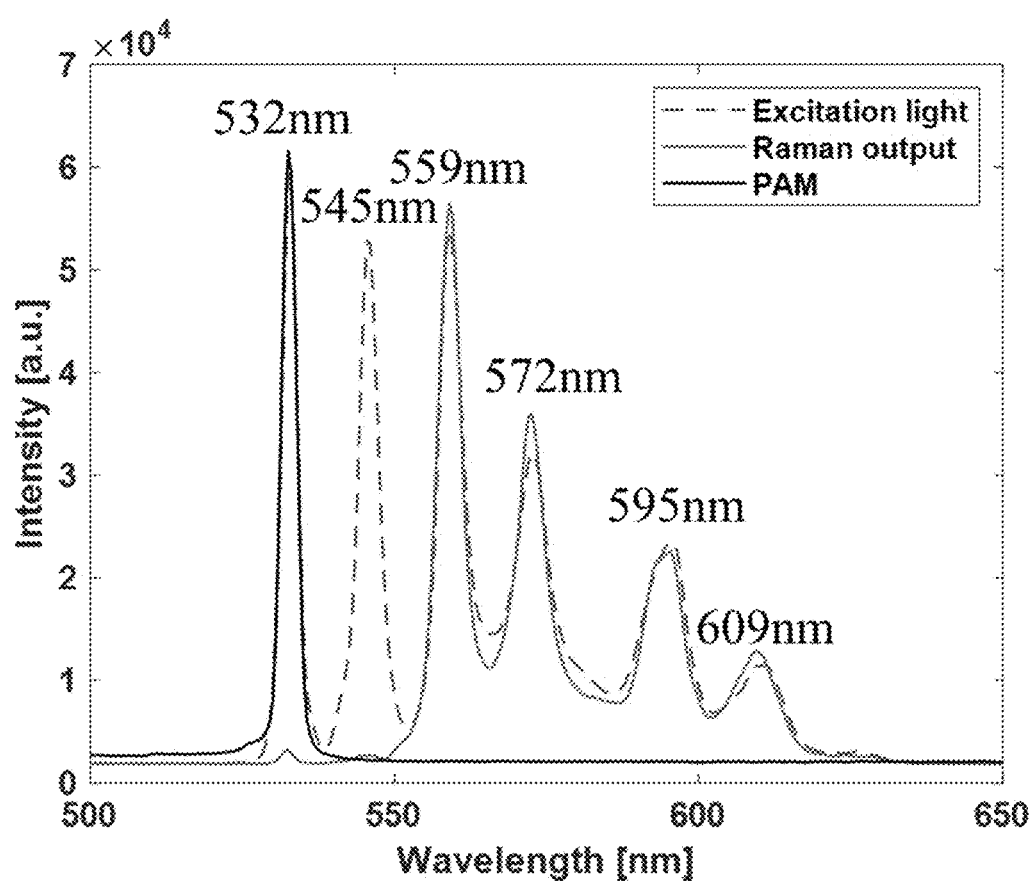
FIG. 6 shows a Raman shift wavelength using spectrum photometer for the second exemplary embodiment.

FIG. 5 shows the experimental setup for simultaneous multi-modality retinal imaging. The details regarding previous multi-modality imaging systems can be found in the following references which are herein incorporated by reference [21, 22]. The prior systems were significantly revised and upgraded so that simultaneous multi-modality imaging became possible. The output of the SPOT-10-532 laser capable of pulse repetition rate (PRR) up to 30 kHz was coupled with a 3 m polarization-maintaining single-mode fiber (PM-SMF) through a fiber collimator[23]. Raman shift of the wavelength in PM-SMF was applied to tune the 532 nm output to a longer wavelength as the illumination source for PAM. The OPO laser (NT-242, Ekspla, Vilnius, Lithuania) was used as the illumination source for FM. With a tunable wavelength from 405-2600 nm, the OPO laser based FM is compatible with numerous fluorescent dyes. The illumination sources for PAM and FM were coaxially aligned through a dichroic mirror (DM1 in FIG. 5, FF556-SDi01-25x36, Semrock). All the wavelengths below 556 nm in the PAM illumination source were removed by a dichroic mirror to avoid interference with fluorescence imaging. The generated stimulated Raman scattering (SRS) peak, the excitation wavelength, and the spectrum of PAM illumination source were measured by a spectrum photometer, shown in FIG. 6.

A triple-edge standard epi-fluorescence dichroic beam splitter (DM2 in FIG. 5, FF395/495/610-Di01, Semrock) placed before integration with the OCT light was used to couple the excitation lights of PAM and FM. The emission of FM directly went through the beam splitter and was detected by an avalanche photodiode. With the wavelength from 795 nm to 1005 nm, OCT illumination light (Ganymede-II-HR, Thorlabs) was coaxially aligned with PAM and FM excitation light before the galvanometer through dichroic mirror (DM3 in Fig.5, FF775-Di01-25x36, Semrock). Here, the light from different imaging modalities was coaxially aligned to ensure co-registration of the multi-modality images. Sharing the same galvanometer, the excitation lights of different modalities were delivered and focused on the same area of the retina through a telescope configuration.

Both the emission light for FM and the reflection light for OCT travelled back to the telescope configuration and galvanometer. The OCT reflection light from the sample directly went through the third dichroic mirror, and combined with the reference light from the reference arm to provide interference, which was detected with the OCT detection system with up to 35-kHz repetition rate. The FM emission light was reflected by a third dichroic mirror and directly went through the triple-edge standard epi-fluorescence dichroic beam splitter. After passing through the fluorescence filter, it was collected by an avalanche photodiode (APD) and then digitized by the DAQ card (PX1500-4, Signatec Inc, Newport Beach, Calif.) with a 300-MHz sampling rate.

The acoustic wave induced by PAM illumination light was acquired by a needle-shaped ultrasound transducer with central frequency of 30 MHz (Optosonic Inc., Arcadia, Calif., USA). The detected signal was amplified by a 57-dB low-noise amplifier (AU-1647, L3 Narda-MITEQ, NY) before digitization. Simultaneously, the laser output energy for both FM and PAM illumination was acquired by a photodiode (PD) and digitized using the same DAQ Card with the same sampling rate.

Both the PAM laser system and OCT system were working in external mode. A four-channel delay generator (DG535, Stanford Research Systems) triggered by the synchronization signal from the OPO laser with a 1 kHz pulse repetition rate was used to precisely trigger the SPOT laser, OCT system, galvanometer, and DAQ card. With a scanning area of 256*256 points, it takes about 68 s to obtain the three modality images.

The lateral resolutions of PAM and SD-OCT were previously quantified to be 4.1 and 3.8 μm, respectively, whereas, the quantified axial resolutions of PAM and OCT were 37.0 μm and 4.0 respectively[21, 22]. In this example, a continuous wave (CW) laser with a central wavelength of 900 nm and a laser energy of 0.95 mW in front of the cornea were applied for OCT. A laser wavelength of 556-620 nm and a laser energy of 80 nJ per pulse before the eye were used for PAM, and a laser wavelength of 480 nm and a laser energy of 2 nJ per pulse were utilized for FM. According to the ANSI safety limit for ocular exposure, the laser energy used for PAM and FM should not exceed 160 nJ, while the laser energy for OCT should be less than 1 mW[24]. All three different modalities in this study were working below the ANSI safety limits.

3D Image Fusion 3D image fusion was performed online by using the simultaneous multi-modality imaging data. The three modalities images were imported to Amira to perform image fusion. Due to coaxially aligned illumination lights for different modalities, the XY plane of three modalities images were naturally coregistered. A 3D fusion image was obtained by simply adjusting the Z-axial position of each modality, where the Z-axial of the OCT image was regarded as the gold standard for its high axial resolution. In a 3D fusion image, the OCT image and the PAM angiography image were combined in 3D, while the 2D FM image was placed on the top of the fusion image.

Animal Preparation

All the experimental procedures were performed in accordance with the ARVO (The Association for Research in Vision and Ophthalmology) Statement for the Use of Animals in Ophthalmic and Vision Research and were approved by the Institutional Animal Care & Use Committee (IACUC) of the University of Michigan (Protocol PRO00008566, Photoacoustic & Molecular Imaging of the Eye). Six New Zealand rabbits (both genders, 2-4 months, 2.0-3.0 kg) were involved in this example. Three different modality images of the retina in the rabbits were imaged in vivo. The rabbits were anesthetized with a mixed solution of ketamine (40 mg kg$^{-1}$) and xylazine (5 mg kg$^{-1}$) by intramuscular (IM) injection. The pupils of the eyes were dilated with 2.5% phenylephrine hydrochloride and 1% tropicamide ophthalmic solution. Topical anesthesia was used by 0.5% topical tetracaine drops prior to initiation of the experiments. A vaporized isoflurane anesthetic (1.5% isoflurane) (Surgivet, MN, USA) and a V-Gel® (D10004, Jorgensen Laboratories, Loveland, CO) were used to maintain anesthesia. A V8400D Capnograph & SpO2 Digital Pulse Oximetry (MWI Animal Health, Boise, Idaho) was utilized to evaluate anesthesia level and continuous monitoring of the heart rate and respiratory rate. Rectal temperature was measured every 15 min. A water-circulating heating pad (TP-700, Stryker Corporation, Kalamazoo, Mich.) was used to keep the body temperature stable. To avoid corneal dehydration and ensure coupling to the ultrasound transducer, balanced salt solution (BSS, Altaire Pharmaceuticals, Inc., Aquebogue, N.Y.) was applied liberally to the eye surface. For the FM imaging, fluorescein sodium (10%, 0.1 mL kg$^{-1}$, Akorn Inc, Lake Forest, Ill.) was intravenously administered through the marginal ear vein.

To evaluate the performance of the multi-model system, rabbits with different clinically relevant retinal disease models were involved in this study, including retinal detachment, retinal vein occlusion, and choroidal neovascularization. To create the rabbit retinal vein occlusion, Rose Bengal (Sigma, St. Louis, Mo., USA) with concentration of 50 mg/mL was administrated intravenously through the marginal ear vein with a sustained-release injection with a total volume of 3 mL[25, 26]. During the injection, an argon green laser light (Vitra 532 nm, Quantel Medical, Cournon d'Auvergne, France) was used to treat the main retinal veins with 10 shots for each vein (150 mW, 75 μm, 500 ms) until the blood vessel was completely occluded and the blood flow was stopped. Retinal detachment was induced by intravitreal injection of DL-α-aminoadipic acid (AAA) leading to chronic retinal neovascularization. A single intravitreal injection in one eye with 50 μL of 0.025 M DL-AAA whereas 50 μL of saline was injected to wild type New Zealand white rabbits[27]. Fundus photography and FA were used to follow the changes in the rabbit retina until the pathological changes occur.

Results

Normal Retinal Blood Vessel

Figure 7:
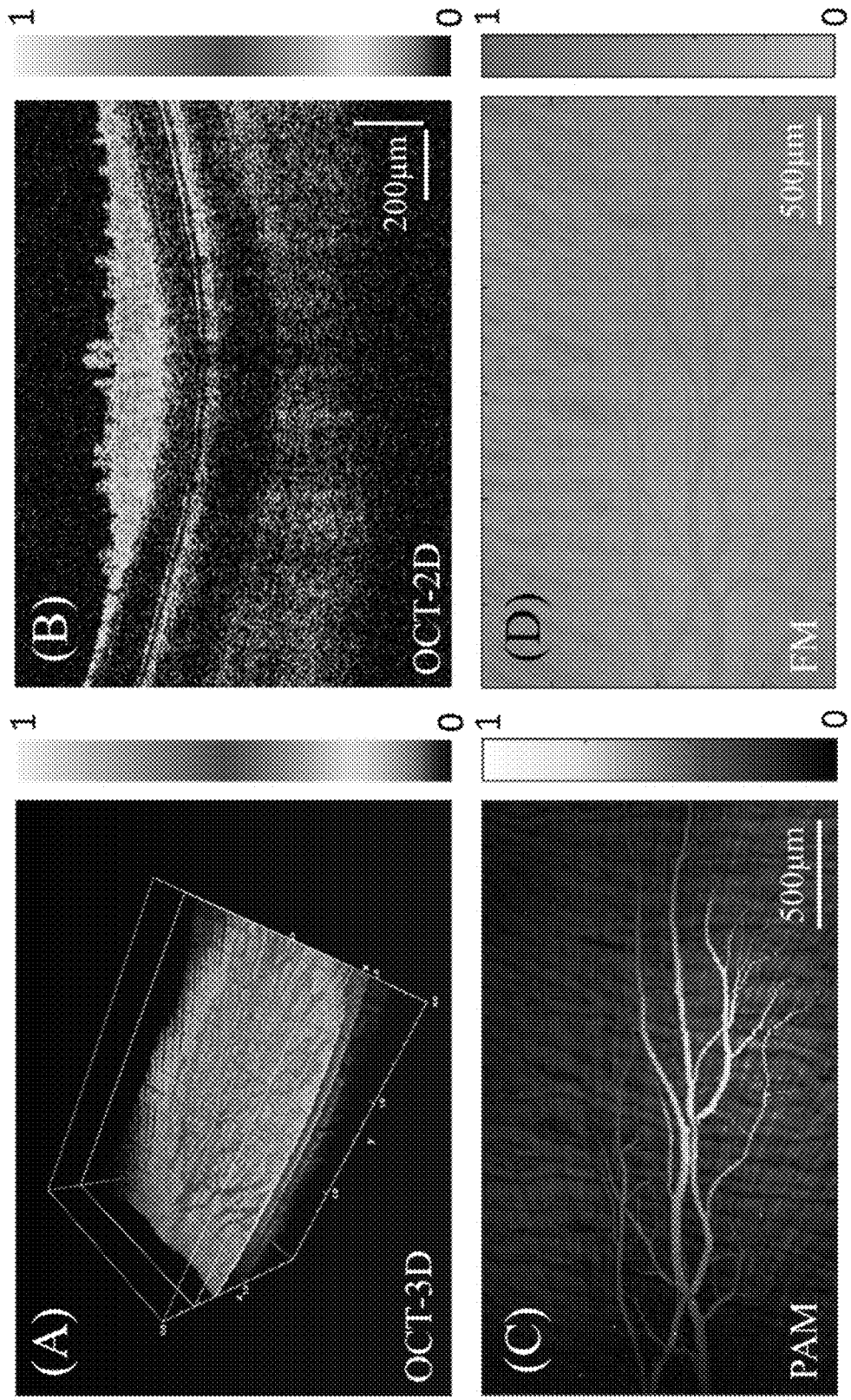
FIG. 7 shows multi-modality simultaneous images of the retina in a normal rabbit eye using the second exemplary embodiment. (A) The side view of 3D OCT image; (B) The 2D cross-section view of OCT image; (C) The peak-value projection of PAM image; (D) 2D FM image.

The results in FIG. 7 show the three different modality images of the normal rabbit retinal and choroidal blood vessels. As shown in FIG. 7(A), the 3D structure of whole retina can be obtained through OCT en-face image. The different layers of the retina can be clearly distinguished on OCT B-scan images. In the PAM image shown in FIG. 7(C), high resolution angiography imaging is obtained of the distribution of the retinal and choroidal blood vessels. As shown in FIG. 7(D), the circulation of the fluorescein dye was indicated by FM imaging.

Retinal Detachment

Figure 8:
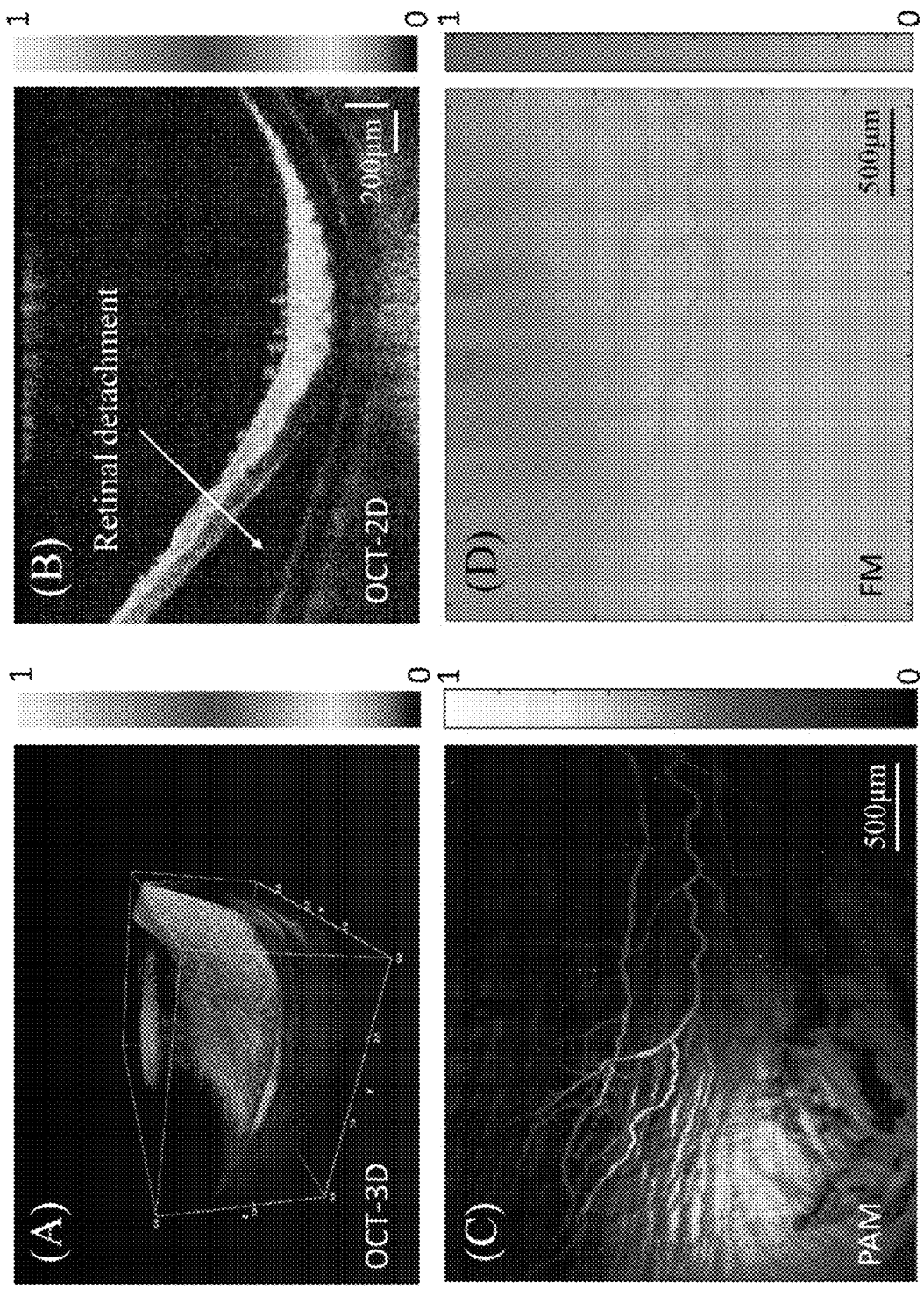
FIG. 8 shows multi-modality simultaneous images of retinal detachment in the rabbit eye using the second exemplary embodiment. (A) The side view of 3D OCT image; (B) The 2D cross-section view of OCT image; (C) The peak-value projection of PAM image; (D) 2D FM image.

The retina detachment was generated 2 weeks after the intravitreal injection of DL-AAA. Multi-modality simultaneous imaging was performed after the retinal detachment occurred. As shown in FIG. 8(A) and FIG. 8(B), the retinal detachment can be clearly distinguished. OCT imaging precisely indicates the subretinal fluid between the neurosensory retina and the retinal pigment epithelium (RPE) layer and provides quantifiable volumetric data. In FIG. 8(C), PAM shows the vasculature of the retina and choroid. Due to the high contrast provided by hemoglobin, the hemorrhage can be distinguished clearly in the PAM image. Although PAM can display differences between the normal retina and retinal detachment, it provides limited information on the retinal detachment. Fluorescein angiography provides the vasculature circulation information and provides limited information regarding the retinal detachment.

Retinal Vein Occlusion Complicated by Choroidal Neovascularization

Figure 9:
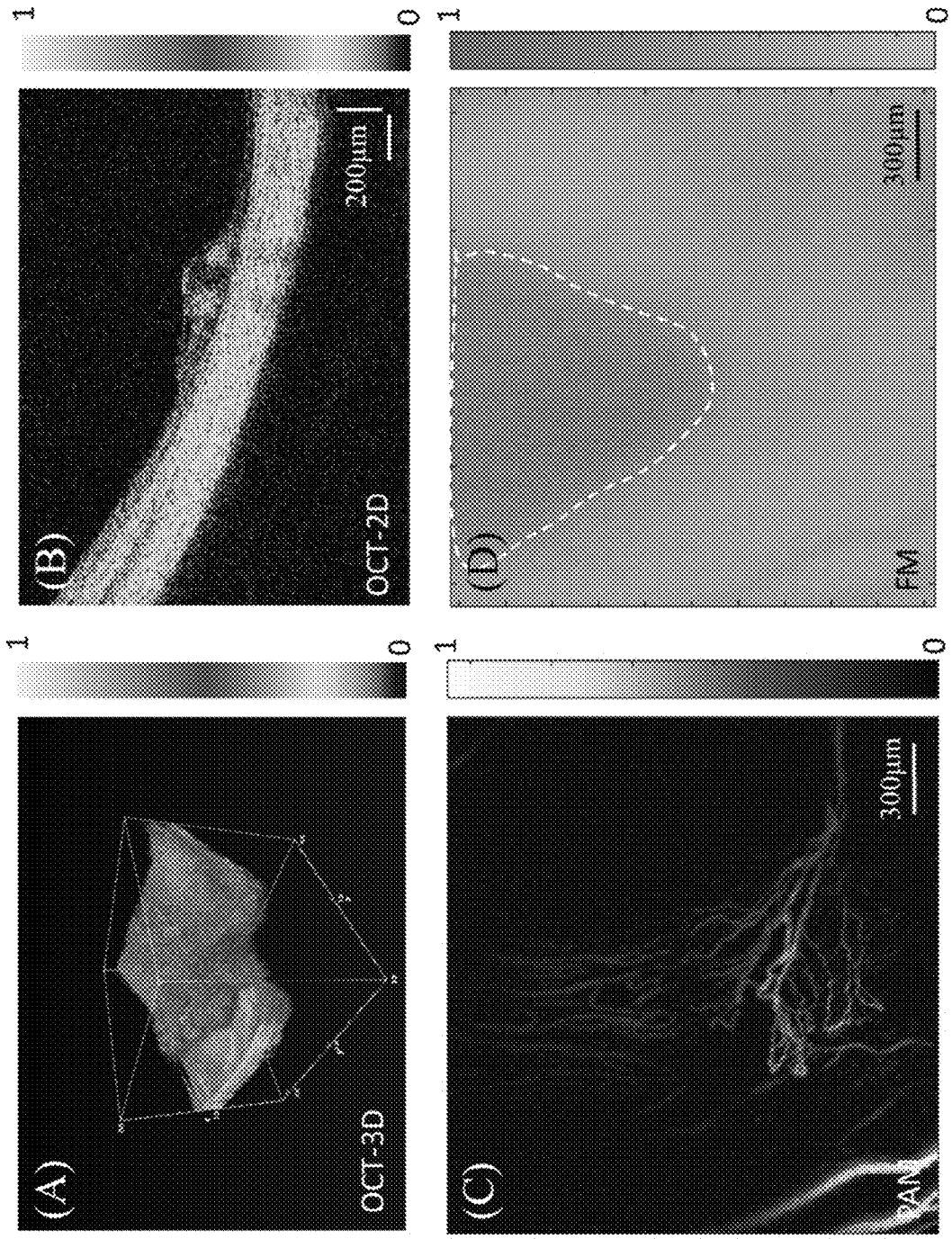
FIG. 9 shows multi-modality simultaneous images of choroidal neovascularization in rabbit eye using the second exemplary embodiment. (A) The side view of 3D OCT image; (B) The 2D cross-section view of OCT image; (C) The peak-value projection of PAM image; (D) 2D FM image. (The white dashed area indicates the fluorescein leakage area).

Choroidal neovascularization (CNV) was generated one month after creating the RVO disease model. Imaging was taken 5 weeks after model creation. As shown in FIG. 9(A) and FIG. 9(B), OCT images demonstrate significant retinal atrophy, with thinning of the neurosensory retina particularly the inner retina. The vasculature is hard to distinguish on OCT images. Although we still can see the nerve fiber layer above the retina, the retinal blood vessels are absent. According to the PAM image shown in FIG. 9(C), the newly generated retinal vasculature can be clearly imaged, while the information of choroidal blood vessels located at the left side of the retinal blood vessels can be obtained. The difference of characteristic between two kinds of vasculature cannot be distinguished by the PAM image. The patterns of hyperfluorescence and stereoscopic FM images yield valuable information about the leakage of fluorescein dye from retinal and choroidal vessels or through abnormal retinal pigment epithelium, which indicates the position of neovascularization. In FIG. 9(D), although the FM cannot provide a high resolution and high sensitivity image of vasculature in rabbit retina, the leakage property of the neovascularization was clearly demonstrated. With the information from FM and PAM angiography images, both the high-resolution structure information and leakage property of the vasculature in rabbit eye can be obtained.

Figure 10:
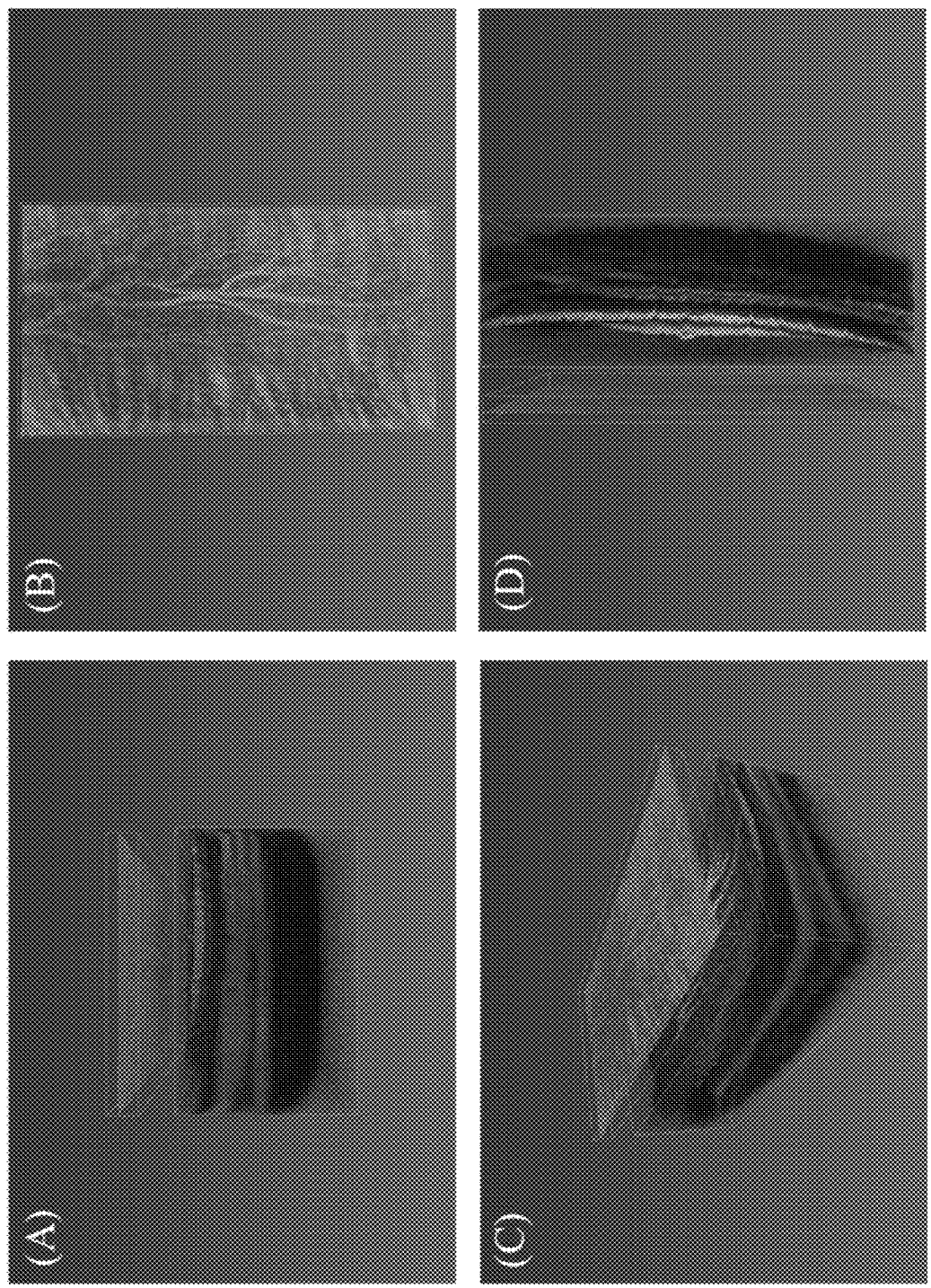
FIG. 10 shows a 3D fusion image of simultaneous multi-modality imaging using the second exemplary embodiment. (A)-(D) Multi-angle view of 3D fusion image with normal rabbit retina.(Red color represents the PAM image, gray color indicates the OCT imaging, and the green color shows the FM image).
Figure 11:
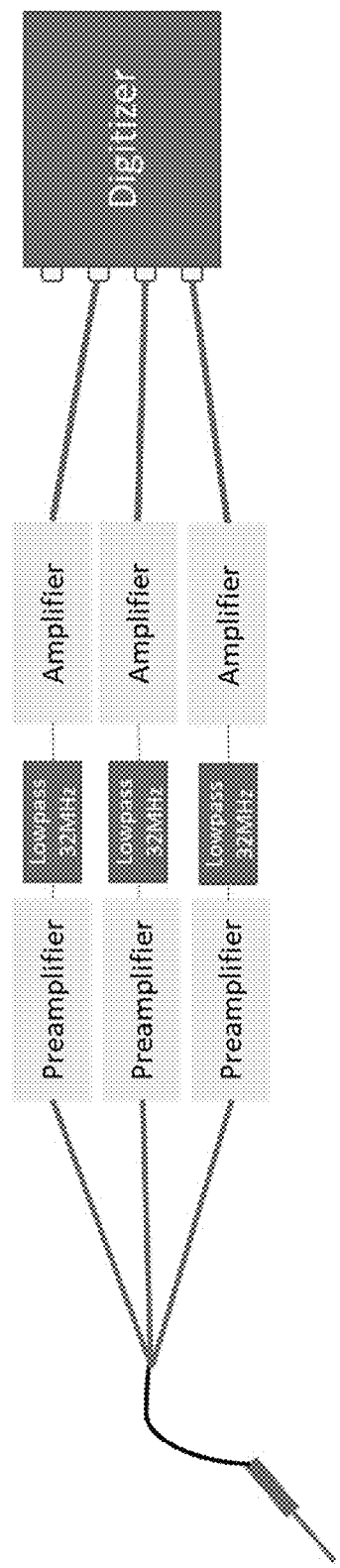
FIG. 11 shows an alternative embodiment to having the same signal going into all three channels of the DAQ (e.g., using a BNC splitter used to split the signals). In particular, in the alternative embodiment, the signal is split before entering the first and then second amplifier as shown in this figure. For example, the signal after the transducer is split into 3 signals, and each of them will go into independent pair of amplifiers (and three independent filters). The amplified signals will go into the three input channels of the DAQ card, respectively. A such, in certain embodiments, the "first amplifier" is three first amplifiers, the "second amplifier" is three second amplifiers, and the "filter" is three filters.

3D Image Fusion 3D image fusion of different modalities was applied with different disease models. By simply adjusting the Z-axial of different modality, the results are shown in FIG. 10. The integrated 3D fusion image shows the retina structure from OCT in gray scale, PAM angiography information with red color, and FM information in green color.

For the normal rabbit retina shown in FIG. 10(A)-(D), the fusion image provides the 3D multi-layer of retina with OCT image, 3D angiography information with PAM image, and 2D circulation of fluorescein dye with FM image. For the retinal detachment, the reduced fluorescence signal shown in the retinal detachment area is consistent with the defocus caused by the retinal detachment. Although the distance between the detached retina and the choroidal layer is indicated by OCT, the PAM angiography image also shows the abnormal distance between retinal blood vessels and choroidal blood vessels in the detachment area. For the choroidal neovascularization model shown, the 2D FM image clearly indicates the leakage area, which is corresponding with the location of the neovascularization. Although the OCT cannot show the small neovascularization, the fusion image with PAM can provide high resolution angiography image. Rather than providing the 2D position of neovascularization by FM, the 3D positioning of neovascularization can be obtained with the 3D structure information of the OCT image.

This example describes a fully-integrated simultaneous multi-modality imaging system combining OCT, PAM, and FM which was tested in vivo in clinically-relevant rabbit eye models. Compared with previous multi-modality imaging system, the newly proposed design is able to achieve simultaneous multi-modality imaging. To avoid the interference of illumination of different modalities, the wavelength of PAM is first shifted to above 550 nm, which is beyond both the excitation spectrum and emission spectrum of fluorescein dye. The OCT is performed in the near-infrared window with CW light, and its wavelength is far away from the PAM and FM illumination lights. Three different lights are combined together through a dichroic mirror. With the illumination lights of different modalities aligned coaxially before the scan head and sharing the same galvanometer system, the XY plane of three modalities images are naturally coregistered. Compared with sequential multi-modality imaging, which perform image registration by using image stretching and image warping to eliminate the misalignment, this system can image the same area with different modalities without interrupt by motion artifact caused by the eye fixation time. By simply adjust the Z-axial position, different modalities can be registered in 3D.

Multi-modality imaging provides unique advantages to visualize anatomic and functional information of diseases. OCT allows for excellent visualization of the different retinal layers with high axial resolution. Due to the lower scattering contrast between the retinal layer and neovascularization, OCT is unable to distinguish the small neovascularization, especially when retinal atrophy is present. Although OCTA can provide high resolution angiography imaging, it cannot provide the information of hemorrhage without blood flow or slow blood flow situations like microaneurysms. Based on the optical absorption properties of tissue, PAM can selectively image blood vessels of the retina and choroid, and bleeding with a higher depth of penetration than OCT with hemoglobin as an endogenous absorber. The high resolution and high sensitivity angiography can be achieved even with retinal atrophy, retinal detachment, and preretinal fibrovascular membranes. FM adds additional information by demonstrating the leakage of neovascularization with fluorescein dye, which is the gold standard to validate neovascularization in retina clinics. By performing simultaneous multi-modality imaging, the three modalities images can be easily fused in a single 3D image. In the resulting fusion image, the location of the vasculature and their leakage properties can be directly visualized. OCT, PAM, and FM all give unique anatomic and functional information which complement one another to provide detailed imaging information of the retinal state and function with excellent agreement observed in fusion images.

The current example involves spectral domain OCT imaging, but OCTA can also be integrated into the simultaneous imaging system. OCTA acquires the variation in OCT signal caused by moving particles through multiple B-scans in the same location. Since all the modalities are working in external mode, integrated OCTA can be achieved by precisely controlling the timing sequence of the different modalities. Meanwhile, the functional PAM with oxygen saturation and blood flow measurement can be integrated with different timing sequences. Photoacoustic oxygen saturation measurements are based on using dual-wavelengths to measure the concentration of oxygenated hemoglobin and deoxyhemoglobin. To achieve this function, two different wavelengths can be used to replace the current photoacoustic illumination light in the future.

Multi-modality imaging can combine the merits and compensate for the limitations of each modality to give additional information that cannot be gleaned from a single modality and can be very beneficial in the field of ophthalmology and other imaging. Simultaneous imaging with OCT, PAM, and FM ensures co-registration of the three modalities without being affected by the motion caused by eye motion and saccades.

REFERENCES (1ST EXEMPLARY EMBODIMENT)

[1] Ng and Lanigan, Journal of pediatric ophthalmology and strabismus, vol. 43, no. 2, pp. 85-90, 2006.
[2] Kumar et al., Journal of visualized experiments: JoVE, no. 84, 2014.
[3] Yang, et al., Photochemistry and photobiology, vol. 81, no. 2, pp. 215-237, 2005.
[4] Podoleanu et al., Br J Radiol, vol. 78, no. 935, pp. 976-88, November 2005.
[5] Sharp, et al., Physics in Medicine & Biology, vol. 49, no. 7, p. 1085, 2004.
[6] Yao and Wang, Laser Photon Rev, vol. 7, no. 5, September 1 2013.
[7] Wang et al., Nature biotechnology, vol. 21, no. 7, pp. 803-806, 2003.
[8] Zhang et al., Light Sci Appl, vol. 7, p. 103, 2018.
[9] Liu and Zhang, Photoacoustics, vol. 4, no. 3, pp. 112-123, 2016.
[10] Song et al., Scientific reports, vol. 4, 2014.
[11] Tian et al., Optics express, vol. 25, no. 14, pp. 15947-15955, 2017.
[12] Elsner and Muller, Laser & photonics reviews, vol. 2, no. 5, pp. 350-376, 2008.
[13] Organisciak and Vaughan, Progress in retinal and eye research, vol. 29, no. 2, pp. 113-134, 2010.
[14] Tian et al., J Vis Exp, vol. 132, no. 132, p. e57135, Feb. 8, 2018.
[15] ANSI, "American National Standard for Safe Use of Lasers ANSI Z136. 1-2014," 2014.
[16] Al-Amri et al., Optics in Our Time. Springer International Publishing, 2016.
[17] K. Schulmeister, S. Althaus, U. Grabner, and G. Vees, "Location and size of the apparent source for laser and optical radiation ocular hazard evaluation."

REFERENCES—SECOND EXEMPLARY EMBODIMENT

[1] Liu and Zhang, Photoacoustic imaging of the eye: a mini review. Photoacoustics, 4 (2016) 112-123.
[2] Ng and Lanigan. Journal of pediatric ophthalmology and strabismus, 43 (2006) 85-90.
[3] Manivannan et al., American journal of ophthalmology, 140 (2005) 525-527.
[4] Kumar et al., Journal of visualized experiments: JoVE, (2014).
[5] Slakter et al., Current opinion in ophthalmology, 6 (1995) 25-32.
[6] Yang et al., Photochemistry and photobiology, 81 (2005) 215-237, 2005.
[7] Podoleanu et al., Optical coherence tomography. Br J Radiol, 78 (2008) 976-988.
[8] Schmitt, Optical coherence tomography (OCT): a review. IEEE Journal of selected topics in quantum electronics, 5 (1999) 1205-1215.
[9] Sharp, et al., Physics in Medicine & Biology, 49 (2004) 1085.
[10] De Carlo et al., A review of optical coherence tomography angiography (OCTA). International journal of retina and vitreous, 1 (2015) 5.
[11] Holz and Spaide, Medical retina: Focus on retinal imaging. Springer Science & Business Media, Berlin, 2010.
[12] Mrejen, Multimodal imaging of pigment epithelial detachment: a guide to evaluation. Retina, 33 (2013) 1735-1762.
[13] Rosin et al., Multimodal retinal imaging: new strategies for the detection of glaucoma. International Conference on Image Processing, 3 (2002) III-III.
[14] Liu et al., Optics letters, 40 (2015) 13701373.
[15] Zaidi and Prasad., Journal of medical physics/Association of Medical Physicists of India, 34 (2009) 122.
[16] Martí-Bonmatí, Multimodality imaging techniques. Contrast media & molecular imaging, 5 (2010) 180-189.
[17] Mujat, et al., Optics express, 18 (2010) 11607-11621.
[18] Estorch and Carrio, Future challenges of multimodality imaging, in Molecular Imaging in Oncology, Berlin, Springer, 2013, pp. 403-415.
[19] Li and Zhu, A new algorithm of multi-modality medical image fusion based on pulsecoupled neural networks, in International Conference on Natural Computation, Springer, 2015 pp. 995-1001.
[20] Zhu, et al., Information Sciences, 432 (2018) 516-529, 2018.
[21] Zhang, et al., Light Sci Appl, 7 (2018) 103.
[22] Tian, et al., Optics express, 25 (2017) 15947-15955.
[23] Hajireza et al., Biomedical optics express, 5 (2014) 539-546.
[24] American National Standards Institute, American national standard for safe use of lasers. Laser Institute of America, 2007.
[25] Ameri et al., Graefe's Archive for Clinical and Experimental Ophthalmology, 246 (2008) 1429.
[26] Nguyen et al., Scientific reports, 9 (2019) 1-14, 2019.
[27] Li, et al., Experimental eye research, 174 (2018) 98-106.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A system comprising:
   a) a laser light source configured to generate an initial nanosecond pulsed laser beam (initial low-energy NPLB), wherein said initial low-energy NPLB is at a pulse energy level of between 1.0 nJ and 7.0 nJ;
   b) a beam splitter configured to split said initial low-energy NPLB into a transmitted low-energy NPLB and a reflected low-energy NPLB;
   c) a focusing assembly configured to direct said reflected low-energy NPLB into a designated area on or inside an object thereby causing localized thermoelastic expansion which generates ultrasonic waves;
   d) an ultrasonic transducer configured to detect said ultrasonic waves and generate a detected signal;
   e) a first amplifier that is a low-noise amplifier configured to amplify said detected signal to generate a first-amplified signal;
   f) a second amplifier configured to amplify said first-amplified signal to generate a second-amplified signal; and
   g) a multi-channel data acquisition system (DAQ) comprising first, second, and third input channels each of which are configured to receive a portion of said second amplified signal such that first, second, and third digital signals are generated.

2. The system of claim 1, further comprising: a processing system operably linked to said DAQ, wherein said processing system comprises: i) a computer processor, and ii) non-transitory computer memory comprising one or more computer programs,
   wherein said one or more computer programs, in conjunction with said computer processor and/or said DAQ, is/are configured to average said first, second, and third digital signals to generate an averaged digital signal.

3. The system of claim 2, further comprising: a photodiode configured to measure the laser energy of said transmitted low-energy NPLD and generate a measured laser energy, and wherein said multi-channel DAQ is operably linked to said photodiode so as to receive said measured laser energy.

4. The system of claim 3, wherein said one or more computer programs, in conjunction with a computer processor and/or said DAQ, is/are further configured to normalize said averaged digital signal using said measured laser energy to generate a normalized digital signal.

5. The system of claim 4, further comprising a median filter configured to generate a filtered signal from said normalized digital signal, and wherein said one or more computer programs, in conjunction with a computer processor and DAQ, is/are further configured to generate at least part of a PAM image from said filtered signal.

6. The system of claim 4, wherein said system is configured to generate a multitude of normalized signals from a multitude of said initial low energy NPLBs, wherein said system further comprises a median filter configured to generate a multitude of filtered signals from said normalized digital signal, and wherein said one or more computer programs, in conjunction with a computer processor and DAQ, is/are further configured to generate a PAM image from said multitude of filtered signals.

7. The system of claim 1, wherein said DAQ further comprises a median filter that is configured to be applied to said normalized signal in the spatial domain.

8. The system of claim 1, wherein said initial low energy NPLB is at a pulse energy level of between 1.5 nJ and 3.3 nJ.

9. The system of claim 1, wherein said initial low energy NPLB is at a pulse energy level of about 3.2 nJ.

10. The system of claim 1, wherein said designated area comprises eye tissue.

11. A method comprising:
   a) activating a beam generating system such that a low-energy reflected nanosecond pulsed laser beam (NPLB) strikes a designated area on or inside an object causing localized thermoelastic expansion which generates ultrasonic waves,
      wherein said low-energy reflected NPLB has a pulse energy level of between 1.0 nJ and 7.0 nJ, and
      wherein said beam generating system comprises:
         i) a laser light source configured to generate an initial low-energy NPLB,
         ii) a beam splitter configured to split said initial low-energy NPLB into a transmitted low-energy NPLB and said reflected low-energy NPLB, and
         iii) a focusing assembly configured to direct said reflected low-energy NPLB into said designated area;
   b) detecting said ultrasonic waves with an ultrasonic transducer to generate a detected signal; and
   c) processing said detected signal with a signal processing system such that first, second, and third digital signals are generated, wherein said signal processing system comprises:
         i) a first amplifier that that is a low-noise amplifier that amplifies said detected signal to generate a first-amplified signal;
         ii) a second amplifier that amplifies said first-amplified signal to generate a second-amplified signal; and
         iii) a multi-channel data acquisition device (DAQ) comprising first, second, and third input channels each of which receive at least a portion of said second amplified signal such that said first, second, and third digital signals are generated.

12. The method of claim 11, wherein said designated area comprises eye tissue.

13. The method of claim 11, further comprising: d) processing said first, second, and third digital signals with a computer processing system operably linked to said DAQ, wherein said computer processing system comprises: i) a computer processor, and ii) non-transitory computer memory comprising one or more computer programs, and wherein said processing comprises averaging said first, second, and third digital signals to generate an averaged digital signal.

14. The method of claim 13, wherein said beam generating system further comprises a photodiode, and wherein the method further comprises: measuring the laser energy of said transmitted low-energy NPLD with said photodiode to generate a measured laser energy.

15. The method of claim 14, wherein said DAQ is operably linked to said photodiode and receives said measured laser energy from said photodiode.

16. The method of claim 15, wherein said one or more computer programs, in conjunction with a computer processor and/or said DAQ, is/are further configured to normalize said averaged digital signal using said measured laser energy to generate an normalized digital signal.

17. The method of claim 16, wherein said normalized digital signal is processed by a median filter to generate a filtered signal, and wherein said one or more computer programs, in conjunction with a computer processor and DAQ, generates at least part of a PAM image from said filtered signal.

18. The method of claim 16 wherein said method is repeated a multitude of times to generate a multitude of normalized signals, wherein said normalized digital signal is processed by a median filter to generate a multitude of filtered signals, and wherein said one or more computer programs, in conjunction with a computer processor and DAQ, generates a PAM image from said multitude of filtered signals.

19. A system for simultaneous multi-modality imaging of an object comprising:
   a) a photoacoustic microscopy (PAM) sub-system comprising a PAM light source configured to generate PAM illumination light;
   b) an optical coherence tomography (OCT) sub-system comprising an OCT light source configured to generate OCT illumination light;
   c) a dye-based microscopy (DbM) sub-system comprising a DbM light source configured to generate DbM illumination light;
   d) a first dichroic mirror configured to coaxially align said PAM and DbM illumination lights;
   e) a dichroic beam splitter configured to couple said PAM and DbM illumination lights;
   f) a second dichroic mirror configured to coaxially align said OCT illumination light with said PAM and DbM illumination lights to generate a combined light,
   g) a galvanometer configured to reflect said combined light;
   h) a telescope assembly configured to deliver and focus said combined light to a designated area on or in an object to generate a PAM initial signal, a DbM initial signal, and an OCT initial signal;
   i) PAM, DbM, and OCT initial signal detectors configured to detect said PAM, DbM, and SD-OCT initial signals, and generate PAM, DbM, and OCT detected signals;
   j) a multi-channel data acquisition (mDAQ) sub-system configured to receive said PAM and DbM, detected signals, and generate PAM and DbM digital signals;
   k) an OCT data acquisition (oDAQ) sub-system configured to receive said OCT detected signal and generate an OCT digital signal; and
   k) a delay generator operably linked to said mDAQ and said oDAQ and configured to be triggered by at least one of said DbM, OCT, or PAM light sources to thereby activate and synchronize: i) the other two of said DbM, OCT, and PAM light sources; ii) said galvanometer, iii) said mDAQ sub-system, and iv) said oDAQ.

20. The system of claim 19, wherein said designated area comprises a dye with a first emission wavelength.

\* \* \* \* \*